Figure 1:
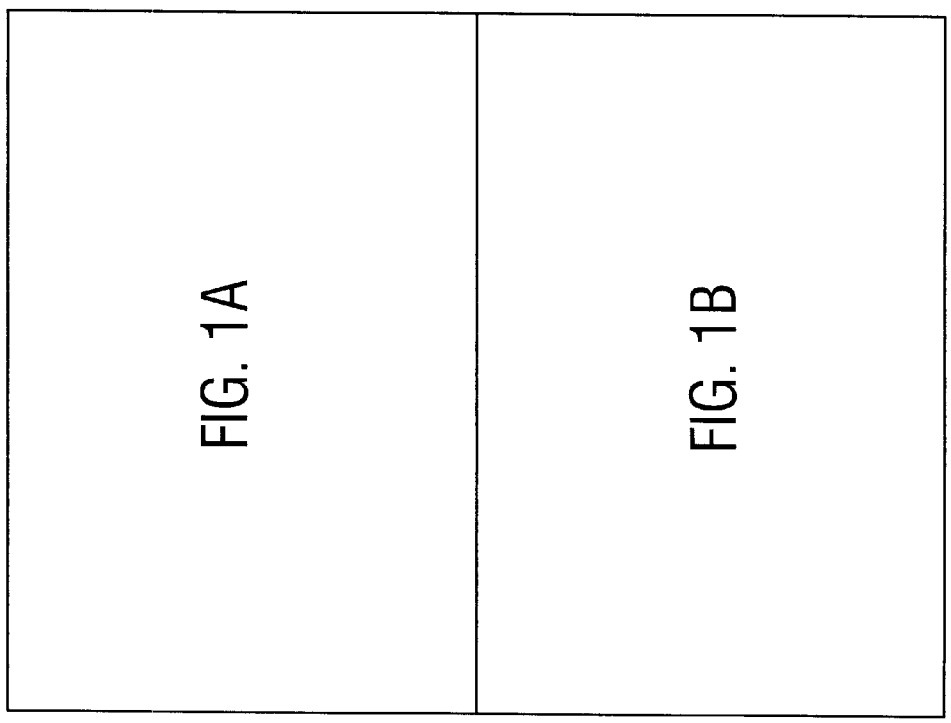

US006296855B1

(12) United States Patent
Hemmen et al.

(10) Patent No.: US 6,296,855 B1
(45) **Date of Patent: *Oct. 2, 2001**

(54) **17-KDA *BRUCELLA ABORTUS* ANTIGEN, RECOMBINANT POLYPEPTIDES, NUCLEIC ACIDS CODING FOR THE SAME AND USE THEREOF IN DIAGNOSTIC AND PROPHYLACTIC METHODS AND KITS**

(75) Inventors: Fabienne Hemmen, Meudon (FR); Eric Saman, Bornem (BE)

(73) Assignee: Innogenetics N.V., Ghent (BE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/849,634

(22) PCT Filed: Nov. 27, 1995

(86) PCT No.: PCT/EP95/04670

§ 371 Date: Dec. 1, 1997

§ 102(e) Date: Dec. 1, 1997

(87) PCT Pub. No.: WO96/17065

PCT Pub. Date: Jun. 6, 1996

(30) Foreign Application Priority Data

Nov. 25, 1994 (EP) ............................................... 94870185

(51) Int. Cl.[7] .......................... A61K 39/02; A61K 39/10; C07K 14/00; C07K 17/00

(52) U.S. Cl. .................................... 424/252.1; 424/234.1; 424/235.1; 424/190.1; 424/184.1; 424/197.11; 424/825; 530/350; 530/300; 530/324

(58) Field of Search ............................. 424/190.1, 184.1, 424/234.1, 235.1, 252.1, 197.11, 825; 530/300, 350, 324

(56) References Cited

U.S. PATENT DOCUMENTS

| | | | | |
|---|---|---|---|---|
| 4,340,588 | * | 7/1982 | Woodard . | |
| 5,023,174 | | 6/1991 | Mayfield et al. | 435/91 |
| 5,188,936 | * | 2/1993 | Tabatabi et al. . | |
| 5,190,860 | * | 3/1993 | Adams et al. . | |
| 5,718,903 | * | 2/1998 | Adams et al. . | |
| 5,939,075 | * | 8/1999 | Houng et al. . | |

FOREIGN PATENT DOCUMENTS

WO88/07374 10/1988 (WO) .

OTHER PUBLICATIONS

Zheludkov et al, Zhurnal Mikrobiologii, Epidemiologii I Immunobiologii 5:74–7 (Abstract Only), Sep.–Oct. 1998.*
De Mot. etal, Current Microbiol, 33: 26–30, 1996.*
Dzata etal, Vet. Microbiol, 29: 15–26, 1991.*
Brooks–Worrell etal, Infection & Immunity 60/6: 2459–2464, 1992.*
Hoffmann etal, J. Clin. Microbiol. 24/5:779–784, 1986.*
Lindler etal, Infection & Immunity. 64/7: 2490–2499, 1996.*
Denoel etal, J. Med Microbiol, 46:801–806, 1997.*
Cloeckaert etal, J. Clin. Microbiol. 30/12: 3168–3174, 1992.*
Denoel etal, Infection & Immunity. 65/2: 495–502, 1997.*
Gupta etal . Med.Sci.Res. 23:59–62, 1995.*
Cloeckaert etal, FEMS Microbiol Letters 140:139–144, 1996.*
Cloeckaert et al., "Protection Conferred on Mice by Monoclonal Antibodies Directed Against Outer–Membrane–Protein Antigens of, " *J. Med. Microbiol.* 34:175–180 (1991).
Tibor et al., "Molecular Cloning, Nucleotide Sequence, and Occurrence of a 16.5–Kilodalton Outer Membrane Protein of *Brucella abortus*with Similarity to PAL Lipoproteins," *Infection and Immunity* 62:3633–3639 (1994).
Cloeckaert et al., "Identification of Seven Surface–Exposed Brucella Outer Membrane Proteins by Use of Monoclonal Antibodies: Immunogold Labeling for Electron Microscopy and Enzyme–Linked Immunosorbent Assay," *Infection and Immunity* 58:3980–3987 (1990).
Halling et al., "Deletion of the BCSP31 Gene of *Brucella abortus* by Replacement," *Infection and Immunity* 59:3863–3868 (1991).
Zygmunt et al., "Purification, Characterization, and Seroactivity of a 20–Kilodalton Brucella Protein Antigen," *Journal of Clinical Microbiology* 30:2662–2667 (1992).
Goldbaum et al., "Characterization of an 18–Kilodalton Brucella Cytoplasmic Protein Which Appears to be a Serological Marker of Active Infection of Both Human and Bovine Brucellosis." *Journal of Clinical Microbiology* 31:2141–2145 (1993).
Hemmen et al., "Cloning and Sequence Analysis of a Newly Identified *Brucella abortus* Gene and Serological Evalation of the 17–Kilodalton Antigen that it Encodes," *Clinical and Diagnostic Laboratory Immunology* 2:263–267 (1995.

* cited by examiner

*Primary Examiner*—Nita Minnifield
(74) *Attorney, Agent, or Firm*—Howrey Simon Arnold & White, LLP

(57) ABSTRACT

The present invention relates to an isolated 17-kDa Brucclla antigen characterized by an amino acid sequence having at least 60% homology, preferably at least 70% homology, more preferably having at least 80% homology to the amino acid sequence as shown in SEQ ID No. 1 or 2, with said antigen being specifically recognized by sera from Brucella field infected individuals, more particulary an antigen characterized by the amino acid sequence as shown in SEQ ID No. 1 or 2. The invention also relates to recombinantly produced 17 kDa Brucella antigen, nucleic acids coding for the same and the use thereof in diagnostic and prophylactic methods and kits.

4 Claims, 7 Drawing Sheets

```
  1 GAATTCCGATCAGTGCATAGTTTCCGCGTGCTCGCGCAATGGTGCGCGGGCTTGTTCTC
 60 GGGGCGGGGTGAAACTCCCCACCGGCGGTATGAAAAGCAATTTTCAAGCCCGGAGCGC
119 CTGAAAATGGAAGCCGATTCGCATGCCATTCAGGGTCAGCAGATCCGGTGAGATGCCGG
178 AGCCGACGGTTAAAGTCCGGATGGAAGAGAGCGAATGAGCGTCACGATTGCGCCTTCCG
237 GCGTCGTCTTGCGTTCTTTTGTGCGCCCTGATTCTAGTTTCGTGAGGAACCTATGAAC
                                                        MetAsn
296 CAAAGCTGTCCGAACAAGACATCCTTTAAAATCGCATTCATTCAGGCCCGCTGGCACGCC
    GlnSerCysProAspLysThrSerPheLysIleAlaPheIleGlnAlaArgTrpHisAla
356 GACATCGTTGACGAAGCGGCAAAAGCTTTGTCGCCGAACTGGCCGCAAAGACGGGTGGC
    AspIleValAspGluAlaAlaLysSerPheValAlaGluLeuAlaAlaLysThrGlyGly
416 AGCGTCGAGGTAGAGATATTCGACGTGCCGGGTGCATATGAAATTCCCCTTCACGCCAAG
    SerValGluValGluIlePheAspValProGlyAlaTyrGluIleProLeuHisAlaLys
476 ACATTGGCCAGAACCGGGCGCTATGCAGCCCATCGTCGGTGCGGCCTTCGTGATCGACGGC
    ThrLeuAlaArgThrGlyArgTyrAlaAlaIleValAlaIleGlyAlaAlaPheValIleAspGly
```

FIG. 1A

536 GGCATCTATCGTCATGATTTCGTGGGCGACGGGCCGTTATCAACGGCATGATGCAGGTGCAG
    GlyIleTyrAspHisAspPheValAlaThrAlaValIleAsnGlyMetMetGlnValGln

596 CTTGAAACGGAAGTGCCGGTGCTGAGCGTCGTGCTGACGCCGCACCATTTCCATGAAAGC
    LeuGluThrGluValProValLeuSerValValLeuThrProHisHisPheHisGluSer

656 AAGGAGCATCACGACTTCTTCCATGCTCATTTCAAGGTGAAGGGCGTGGAAGCGGCCCAT
    LysGluHisAspPhePheHisAlaHisPheLysValLysGlyValGluAlaAlaHis

716 GCCGCCTTGCAGATCGTGAGCGAGGCAGCCGCATGCCGCGCTTGTCTGACTAACCCTC
    AlaAlaLeuGlnIleValSerGluArgSerArgIleAlaAlaLeuVal

776 TATAATACGCCCGCAATGGGTATAAATGTCGAATTC

FIG. 1B

MVRSSSQNSS DKPVAHVVAN HQVEEQGIHH HHHHVDPMNQ SCPNKTSFKI
AFIQARWHAD IVDEARKSFV AELAAKTGGS VEVEIFDVPG AYEIPLHAKT
LARTGRYAAI VGAAFVIDGG IYRHDFVATA VINGMMQVQL ETEVPVLSVV
LTPHHFHESK EHHDFFHAHF KVKGVEAAHA ALQIVSERSR IAALV

FIG. 3

17-KDA *BRUCELLA ABORTUS* ANTIGEN, RECOMBINANT POLYPEPTIDES, NUCLEIC ACIDS CODING FOR THE SAME AND USE THEREOF IN DIAGNOSTIC AND PROPHYLACTIC METHODS AND KITS

The present invention relates to an isolated and pure 17-kDa *Brucella abortus* antigen, which can be used for the diagnosis of Brucella infection in human and cattle. The invention also relates to nucleic acids coding for said antigen, as well as to diagnostic methods and kits using such nucleic acids for detecting Brucella infection. The invention also relates to recombinant polypeptides, a process for preparing the same and their use in methods and kits for the diagnosis of Brucella infection. The invention also relates to the possible use of said isolated antigen or said recombinant polypeptides as an active principle of a vaccine composition against Brucella strains. The invention relates also to a vaccine composition comprising a recombinant Brucella strain, specifically deleted for the gene encoding said antigen.

Brucellosis is an infection due to a small intracellular gram-negative bacterium which is pathogenic for humans as well as for domestic animals. This infection induces abortions in livestock animals leading to severe economic losses. Within the genus Brucelia, six closely related species have been described (Fekete et al., 1992; Verger et al., 1985; Verstraete & Winter, 1984), the most important of which are *B. abortus* and *B. melitensis*. Humans and ruminants (sheep, goats and cows) are predominantly infected by these two Brucelia strains. Serological tests currently used for diagnosis of brucellosis infection are based on the detection of anti-lipopolysaccharide (LPS) antibodies (Alton et al., 1988). These tests do not permit the differentiation between vaccinated and infected animals, and fail to reveal some infected animals which are positive in an intradermic test. Moreover important cross-reactions with other gram-negative bacteria have been reported (Corbel et al., 1983; Perry & Bundle, 1990; Schoerner et al., 1990). Diagnostic tests with higher specificity are based on the isolation of Brucella bacteria or on the intradermic injection of a protein preparation from Brucella bacteria "Brucellergen" (Fensterbank, 1984), leading to a delayed type hypersensitivity reaction (DTH). However, classical bacteriology is time-consuming and "Brucellergen" preparations are not always easy to produce free of LPS. The latter can cause seroconversion of animals upon DTH testing, precluding its serological distinction from infected animals. The identification of specific antigens for brucellosis diagnosis is therefore a matter of great interest for the development of a specific serological test.

For prophylactic vaccination against brucellosis, today two live vaccine strains are being used succesfully. The B19 strain is mostly used in cattle and the Rev. 1 strain in small ruminants. The H38 killed vaccine has also been used. Although good protection is generally obtained with these vaccines, the general drawback is the induction of an immune response in the vaccinated animals, which precludes the distinction between infected and vaccinated animals.

A *Brucella abortus* cytoplasmic preparation was described by Goldbaum et al. (1993) which showed several bands of different molecular weights. The two major components are those of 18- and 36-kDa. This cytoplasmic preparation was obtained by immunoadsorption of a *B. abortus* cytoplasmic fraction with an IgG2b monoclonal antibody (BI24) produced by immunizing with a LPS-free cytoplasmic antigenic fraction preparation (LPS-free CYT) as antigen. Microsequencing of the identified cytoplasmic preparation (including the 18- and 36-kDa bands) resulted in the elucidation of the sequence of only the following three tryptic peptides:
(i) SEQ ID NO: 6
(ii) SEQ ID NO: 7
(iii) SEQ ID NO: 8

Another cytoplasmic Brucella protein preparation with an apparent molecular mass of 20 kDa has been described by Zygmunt et al. (1992).

Cloeckaert et al. (1990, 1991) describe the production of 26 anti-Brucella OMP monoclonal antibodies to R and S Brucella cells directed against seven outer membrane protein components.

The aim of the present invention is to provide a Brucella antigen or a polynucleic acid encoding the same which is useful for diagnosing in vitro Brucella infection (=brucellosis) in mammals (humans, ruminants).

A special aim of the invention is to provide a Brucella antigen or a polynucleic acid encoding the same which is useful for differentiating between field infected and vaccinated individuals.

Another aim of the present invention is to provide purified and isolated 17 kDa antigen of Brucelia, and more particularly purified and isolated *B. abortus* 17 kDa antigen.

Another aim of the present invention is to provide amino acid and corresponding nucleotide sequences of said Brucella 17 kDa antigen.

Another aim of the present invention is to provide antibodies specifically directed against said Brucella 17 kDa antigen.

Another aim of the present invention is to provide primers and probes derived from the nucleotide sequences encoding said Brucella 17 kDa antigen.

Another aim of the present invention is to provide diagnostic methods or kits for diagnosing Brucella infection, more particularly for differentiating between field infected and vaccinated individuals, based on any of the above-mentioned polypeptides or polynucleic acids as active compounds.

Another aim of the present invention is to provide vaccine compositions providing protective immunity towards brucellosis in mammals (humans, ruminants).

Another aim of the present invention is to provide a recombinant Brucella strain in which the gene encoding the Brucella 17 kDa antigen has been deleted or inactivated.

The present invention relates more particularly to an isolated 17-kDa Brucella antigen characterized by an amino acid sequence having at least 60% homology, preferably at least 70% homology, more preferably at least 80% homology to the 158 residue amino acid sequence as shown in SEQ ID NO 2, or fragments of said antigen, consisting of at least 9 contiguous amino acids from said amino acid sequence.

The term "isolated" refers to a purity grade of at least 90%, preferably 95% and more preferably of 98% of the antigen expressed in weight versus contaminants, as determined by one or two dimensional SDS-PAGE. Said purity may be obtained by purification of the naturally occurring polypeptide, or by de novo synthesis of the polypeptide, by chemical methods or by recombinant DNA technology, and subsequent purification. The term "isolated" thus implies that the antigen is in a different state and environment than the naturally occurring antigen.

The word "antigen" refers to a molecule which provokes an immune response (also called "immunogen"), or which can be recognized by the immune system (also called "antigen sensu strictu"). The immune response or the immune recognition reaction can be of the cellular or humoral type.

The term "17 kDa antigen" refers to an antigen having a molecular weight of approximately 17 kDa as determined by SDS-PAGE. Said determined molecular weight may vary according to strain to strain variations, or according to methodology variations. Preferably, the molecular weight of the antigen of the invention as determined by SDS-PAGE is between 14 and 20 kDa, more preferably between 15 and 19 kDa, most preferably between 16 and 18 kDa.

The terms "homologous" and "homology" are used in the current invention as synonyms for "identical" and "identity"; this means that amino acid sequences which are e.g. said to be 55% homologous, show 55% identical amino acids in the same position upon alignment of the sequences.

In an effort to identify a purified and isolated Brucella 17-kDa antigen, an expression library containing *B. abortus* chromosomal DNA inserts was screened with sera from field infected sheep (see Examples section). The DNA insert from a positive recombinant phage was analyzed in detail. Sequence analysis revealed a new gene encoding a 17-kDa *Brucella abortus* protein (SEQ ID NO 1). The gene was recombinantly expressed, and the antigenicity of the recombinantly produced new protein was analyzed in Western blotting, in ELISA using sera from infected humans and ruminants (sheep, goats, cows), and in competitive ELISA with a panel of Brucella monoclonal antibodies, to evaluate its significance for serological diagnosis of Brucella infected individuals.

According to a preferred embodiment, the invention relates to a polypeptide or peptide comprising in its amino acid sequence part of the amino acid sequence as represented in SEQ ID NO 2, said part consisting of at least 9 contiguous amino acids of the amino acid sequence represented in SEQ ID NO 2.

In a very specific embodiment the invention relates to an isolated 17-kDa *Brucella abortus* antigen characterized by the 158 residue amino acid sequence as shown in SEQ ID NO 2, or a fragment thereof, said fragment consisting of at least 9 contiguous amino acids of the amino acid sequence represented in SEQ ID NO 2.

The fragments of the above-mentioned polypeptides are preferably more than 8, more preferably more than 9, 10, 11, 12, 13, 14, 15, 16, 17, 18, 19, 20, 25, 30, 35, 50, 55 or 60 amino acids residues long, said amino acids being contiguous amino acids selected from the amino acid sequences of any of the polypeptides described above.

The 17-kDa *Brucella abortus* polypeptide of SEQ ID NO 2, and the corresponding nucleic acid of SEQ ID NO 1, are new.

A preferred embodiment of the present invention relates to any of the polypeptides or polypeptide fragments as described above, with said polypeptides or polypeptide fragments having at least one of the following immunological (antigenic) properties:

- being specifically recognized by sera from Brucella field infected individuals, and/or
- being specifically recognized by the cellular immune response from Brucella contacted individuals, and/or
- being able to elicit a Brucella specific immune response upon vaccination of individuals prone to brucellosis disease.

Of the above-mentioned immunological properties, the specific recognition by sera from field-infected individuals is the most preferential one.

An additional characteristic of some of the polypeptides of the invention is the differential recognition by sera from field-infected individuals as opposed to sera from vaccinated individuals.

The wording "field infected individuals" as used in the current invention refers to individuals which have been infected by the Brucella pathogen, and in which the infection lead to brucellosis disease.

The wording "Brucella vaccinated individuals" as used in the current invention refers to those individuals which have been vaccinated against brucellosis, and in which the vaccination has lead to protection of the individual against active disease and against vertical transmission of the pathogen.

The wording "Brucella contacted individuals" as used in the currrent invention refers to individuals which have been in contact with the Brucella pathogen, said contact possibly leading to subsequent disease, or to subsequent protection.

The expression "specifically recognized by sera from Brucella field infected individuals" refers to the fact that the 17 kDa Brucella antigen of the present invention shows preferentially a positive immunological reaction with sera from Brucella field infected individuals, whereas it shows preferentially no raction with sera from "control" individuals (such as healthy individuals or individuals infected by other pathogens). Thus, sera originating from Brucella field infected individuals are likely to contain antibodies reacting with this antigen, while sera originating from control individuals are likely not to contain antibodies recognizing the 17-kDa Brucella antigen of the invention. This will be demonstrated in the Examples section.

Preferentially, at least 30%, more preferably at least 40%, most preferably at least 50% or even at least 60% of the sera from field infected individuals react with the polypeptides of the invention, while at most 10%, preferably at most 5, and most preferably at most 1% of the sera from control individuals react with the polypeptides of the invention.

It should be understood that, since the above-mentioned reactivities are usually a result of optical density measurements, e.g. in a standard ELISA assay, positive and negative values have to be considered against a so called "cutoff value", which is not an absolute value, but which can be calculated from the optical density values of the control sera (e.g. cutoff value=mean optical density of the control sera+2 (or 3) standard deviations). This is demonstrated further in the examples section.

The term "individual" refers to an animal or human being liable to be infected by Brucella (species). Brucellosis infects mammals, mostly humans and ruminants.

The expression "to elicit a Brucella specific immune response" refers to the fact that said 17 kDa Brucella immunogen according to the invention is able to give rise to the production of antibodies which are specific for Brucella, or that the 17 kDa Brucella immunogen elicits a cellular immune response specific for Brucella, in individuals liable to be infected by Brucella (species).

The expresssion "specifically recognized by the cellular immune response" throughout the current application refers to the recognition of the polypeptides of the invention by the T-cell population of the Brucella contacted individuals, said recognition being detectable in vitro e.g. by lymphoproliferation tests in presence of the polypeptides of the invention, or in vivo e.g. by a delayed type hypersensitivity reaction upon subcutaneous injection of the polypeptides of the invention in the individual.

As disclosed above, the present invention also relates to antigens characterized by an amino acid sequence showing a homology of at least 60%, preferably at least 70%, and even more preferably at least 80% or 90% to the amino acid sequence of the new *Brucelia abortus* protein as depicted in SEQ ID NO 2. Said "related" antigens may also be referred to as "muteins" of the protein shown in SEQ ID NO 2. The term "muteins" may be defined as proteins containing substitutions and/or deletions and/or additions of one or several amino acids, provided that said muteins have retained the antigenic/immunogenic properties of the Brucella proteins of the invention, i.e.:

being specifically recognized by sera from Brucella field infected individuals, and/or being specifically recognized by the cellular immune response from Brucella contacted individuals, and/or being able to elicit a Brucella specific immune response upon vaccination of individuals prone to brucellosis disease.

An overview of the amino acid substitutions which could form the basis of such muteins are given in Table 1.

Said "muteins" may be the result of strain to strain variations of the Brucella (species) 17 kDa antigen, or may be the result of modifications introduced in the original polypeptide sequences, said modifications bringing about a desirable side effect to the polypeptide molecule (e.g. better physicochemical properties, more efficient purification, more efficient coating characteristics, more stable etc . . . ).

The 17 kDa antigen of *Brucella abortus*, represented by SEQ ID NO 2, has homologous counterparts in other Brucella species, like e.g. *Brucella melitensis, Brucella ovis, Brucella suis*, etc. These homologous genes and proteins are also part of the present invention.

All polypeptides according to the present invention, including muteins and homologues, will be further referred to as "Brucella 17 kDa antigen".

It should also be evident that such muteins and homologues, although falling within the above-given definitions, might have a molecular weight which is slightly different from 17 kDa as determined by SDS-PAGE.

Peptides according to the present embodiment of the invention can be readily determined by the person skilled in the art by applying any of the techniques teached in the Examples and Description sections of the present invention or any other immunological and epitope mapping techniques known in the art.

According to an even more preferred embodiment, the present invention relates to peptidic fragments of Brucella 17-kDa antigen being able to distinguish Brucella field infected from Brucella vaccinated individuals upon incubation with sera originating from those individuals.

Preferably the peptides of the invention are different from a peptide with amino acid sequence SEQ ID NO: 8.

The words "polypeptide" and "peptide" are used interchangeably throughout the specification and designate a linear series of amino acids connected one to the other by peptide bonds between the alpha-amino and carboxy groups of adjacent amino acids. Polypeptides can be in a variety of lengths, either in their natural (uncharged) forms or in forms which are salts, and either free of modifications such as glycosylation, side chain oxidation, or phosphorylation or containing these modifications. It is well understood in the art that amino acid sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acids side chains, such as glycosyl units, lipids, or inorganic ions such as phosphates, as well as modifications relating to chemical conversions of the chains, such as oxidation of sulfhydryl groups. Thus, "polypeptide" or its equivalent terms is intended to include the appropriate amino acid sequence referenced, subject to those of the foregoing modifications which do not destroy its functionality.

The polypeptides of the invention, and particularly the shorter peptides, can be prepared by classical chemical synthesis.

The synthesis can be carried out in homogeneous solution or on solid phase.

For instance, the synthesis technique in homogeneous solution which can be used is the one described by Houben-weyl in the book entitled "Methode der organischen chemie" (Method of organic chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL Press, Oxford, 1989).

The polypeptides according to this invention can also be prepared by means of recombinant DNA techniques as described by Maniatis et al., (Molecular Cloning: A Laboratory Manual, New York, Cold Spring Harbor Laboratory, 1982).

According to another embodiment, the invention relates to a polynucleic acid comprising a sequence of at least 10 contiguous nucleotides selected from:

(a) the polynucleic acid sequences which code for any of the polypeptides described above, or (b) the polynucleic acid sequences which are degenerate as a result of the genetic code to the polynucleic acid sequences as defined in (a), and which still encode a polypeptide as described above, or (c) the polynucleic acid sequences which hybridize to any of the polynucleic acids as defined in (a) or (b).

According to yet another embodiment, the present invention relates to a polynucleic acid sequence, in an isolated form, comprising a contiguous sequence of at least 10 nucleotides, more particularly 11, 12, 13, 14, 15, 20 or more contiguous nucleotides selected from any of the polynucleic acid sequences as described here above.

The term "polynucleic acid" refers to a single stranded or double stranded nucleic acid sequence which may contain from 10 nucleotides to the total number of nucleotides of the polynucleotide sequence (such as for instance 20, 30, 40, 50, 60, 70, 80 or more nucleotides). A polynucleic acid which is smaller than about 100 nucleotides in length is often also referred to as an oligonucleotide. A polynucleic acid may consist of deoxyribonucleotides or ribonucleotides, nucleotide analogues or modified nucleotides, or may have been adapted for therapeutic purposes. A polynucleic acid may also comprise a double stranded cDNA clone which can be used for cloning purposes, or for in vivo therapy, or prophylaxis.

The expression "hybridizes to" refers to preferably stringent hybridization conditions, allowing hybridisation between sequences showing at least 70%, 80%, 90%, 95% or more homology with each other.

The expression "in isolated form" refers to the fact that said polynucleic acid is preferably 90%, more preferably 95%, most preferably 98% pure as measured by its weight versus the weight of possible contaminants.

The Brucella polynucleic acids according to this embodiment of the present invention are preferably more than 55% homologous, more preferably more than 65%, and most preferably more than 75% homologous (e.g. more than 85%, more than 90%, more than 95% homologous) to the nucleic acid sequence shown in SEQ ID NO 1.

The terms "homologous" and "homology" are used in the current invention as synonyms for "identical" and "identity"; this means that nucleic acid sequences which are e.g. said to be 55% homologous, show 55% identical basepairs in the same position upon alignent of the sequences.

According to a subsequent embodiment, the invention relates to a polynucleic acid as described above comprising a sequence of at least 10 contiguous nucleotides selected from:

(a) the polynucleic acid sequence as shown in SEQ ID NO 1, or, (b) the polynucleic acid sequences which are degenerate as a result of the genetic code to the polynucleic acid sequences as shown in SEQ ID NO 1, and which still encode a *Brucella abortus* 17-kDa antigen as shown in SEQ ID NO 2, (c) the polynucleic acid sequences which hybridize to the polynucleic acid sequences as defined in (a) or (b).

According to a preferred embodiment, the present invention relates to any nucleotide sequence which, upon expression, gives rise to a polypeptide sequence as represented in SEQ ID NO 2, or part thereof.

Another embodiment of the invention refers to a polynucleic acid as described above being comprised in a cDNA or a genomic clone, with said clone being obtainable by a process comprising essentially the following steps:

(a) preparing a Brucella species genomic library and/or expression library, by digestion of chromosomal DNA of said Brucella species and ligation in an appropiate cloning and/or expression vector, and, (b) immunoscreening said Brucella species expression library with Brucella field infected individuals sera, or with antibodies raised against any of the polypeptides of the invention described above, and/or (c) screening said Brucella species genomic library with a probe hybridizing specifically with a polynucleic acid of the invention as described above, and (d) characterizing the positive clones obtained in the screening steps of (b) and/or (c) by means of sequence analysis, after the insert of the obtained clones has been isolated and possibly amplified by means of PCR, and (e) possibly repeating step (c) and (d) using the obtained amplified material as a probe to isolate the complete gene, and characterizing the obtained clone by means of sequence analysis.

The term "clone" refers to a population of cells or organisms formed by repeated asexual division from a common cell or organism. To "clone a gene" means to produce many copies of a gene by repeated cycles of replication.

The term "genomic library" refers to a collection of clones, each clone containing a different insert of (c)DNA in a cloning vector, said insert corresponding to a different part of the genome of the respective organism. A "(genomic) expression library" enables the expression of the (c)DNA inserts into polypeptide fragments.

Another embodiment of the invention provides for an oligonucleotide probe comprising part of a polynucleic acid sequence as described above, with said probe being able to act as a specific hybridization probe for detecting the presence of a Brucella polynucleic acid encoding any of the polypeptides as described above, or part thereof.

Preferably said oligonucleotide probe comprises at least 10 contiguous nucleotides, more preferably 11, 12, 13, 14, 15, 16, 17, 18, 19, 20, 25 , 30 or 50 contiguous nucleotides selected from any of the above-mentioned polynucleic acid sequences.

The term "probe" refers to single stranded sequence-specific oligonucleotides which have a sequence which is sufficiently complementary to hybridize to the target sequence to be detected.

Probes according to this aspect of the present invention may be chosen according to any of the techniques known in the art. Probes may be provided hybridizing to Brucella species which cause brucellosis in different kinds of animals and in humans (*B. abortus, B. melitensis, B. ovis, B. suis* . . . ). More particularly, probes specifically hybridizing to certain species of Brucella may be provided. Under appropriate hybridization conditions, such probes may allow to distinguish different Brucella species present in a sample to be analyzed.

According to the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACl solutions (Jacobs et al., 1988).

The latter implies that variant probes contemplated within this aspect of the present invention can be defined as probes hybridizing with the same specificity as the probe they are derived from, possibly under different, but stringent, hybridization and wash conditions (different solutions, different concentrations of buffer, different concentrations of probe, different temperatures).

The oligonucleotides used as primers or probes may also contain or consist of nucleotide analoges such as phosphorothioates (Matsukura et al., 1987), alkylphosphorothiates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention, these variations will necessitate adaptions with respect to the conditions under which the oligonucleotide should be used to obtain the required specificity and sensitivity. However, the eventual results of hybridization will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules. etc.

The term "complement" refers to a nucleotide sequence which is exactly complementary to an indicated sequence and which is able to hybridize to the indicated sequences. It should be clear that all polynucleic acids of the invention, although only represented by one strand, also encompass the other complementary strand. This implies that all probes and primers specified may also be used in their complementary form, be it under different hybridization or amplification conditions.

An oligonucleotide primer comprising part of a polynucleic acid sequence as described above, with said primer being able to initiate specific amplification of a Brucella polynucleic acid encoding any of the polypeptides of the invention as described above, or part thereof.

Preferably said oligonucleotide primer contains at least 10, more preferably at least 11, 12, 13, 14, 15, 16, 17, 18, 19, 20, 21, 22, 23, 24, 25, 26, 27, 28, 29 or 30 contiguous nucleotides of any of the polynucleic acid sequences as described above.

The term "primer" refers to a single stranded DNA oligonucleotide sequence capable of acting as a point of initiation for synthesis of an extension product which is complementary to the nucleic acid strand to be copied. The length and the sequence of the primer must be such that they allow to prime the synthesis of the extension products. Preferably the primer is about 5–50 nucleotides long, more preferably 10–30 nucleotides long. Specific length and sequence will depend on the complexity of the required DNA or RNA targets, as well as on the conditions of primer use such as temperature and ionic strength.

The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) of any other suitable method to amplify nucleic acid molecules using primer extension. During amplification, the amplified products can be conveniently labelled either using labelled primers or by incorporating labelled nucleotides. Labels may be isotopic ($^{32}$P, $^{35}$S, etc.) or non-isotopic (biotin, digoxigenin, etc.). The amplification reaction is repeated between 20 and 80 times, advantageously between 30 and 50 times.

According to a further embodiment, the invention relates to a recombinant vector particularly for cloning and/or expression of any of the polynucleic acids of the invention as described above, with said recombinant vector comprising a vector sequence and at least part of a any of the polynucleic acid sequence as described above, and wherein, in case of a expression vector, the coding sequence of said polynucleic acid sequence is operably linked to a control sequence comprised in the vector sequence and capable of providing for the expression of the coding sequence by the specific host.

The expression "operably linked" refers to a juxtaposition wherein the components are configured so as to perform their usual function. Thus, control sequences operably linked to a coding sequence are capable of effecting the expression of the coding gene.

The term "control sequences" refers to those sequences which control the transcription and/or translation of the coding sequences; these may include but are not limited to the promoter sequences, transcriptional and translational initiation (ribosome binding sites) and termination sequences. In addition, control sequences refer to sequences which control the processing of the polypeptide encoded within the coding sequence; these may include, but are not limited to sequences controling secretion, protease cleavage, and glycosylation of the polypeptide.

The term "recombinant vector" may include a plasmid, a phage, a cosmid or a virus. A variety of vectors may be used to obtain recombinant expression of antigenic proteins. Bacteria are most often transformed by plasmids or bacteriophages. Lower eukaryotes such as yeasts are typically transformed with plasmids, or are transformed with a recombinant virus. The vectors may replicate within the host independently, or may integrate into the host cell genome. Higher eukaryotes may be transformed with vectors, or may be infected with a recombinant virus, for example a recombinant vaccinia virus.

According to an alternative embodiment, the current invention also provides for a recombinant vector particularly for cloning and/or expression of heterologous sequences, with said recombinant vector comprising a vector sequence and the control elements, or parts thereof, comprised in the polynucleic acids of the invention, and wherein, in case of an expression vector, said control elements are operably linked to the coding sequence of the heterologous gene to be expressed.

The term "heterologous sequence" as used in the current invention signifies any sequences different from the 17 kDa Brucella antigen sequences. Said heterologous sequences may also be called "foreign" sequences.

The control sequences comprised in the polynucleic acids of the invention are located in the region upstream of the sequences coding for the polypeptides of the invention.

The invention further relates to a host cell transformed by any of the recombinant vectors described above, with said host cell being preferably a prokaryotic organism, and more preferably E. coli, a Salmonella species or a lactic acid bacterium.

Host cells suitable for the expression of the polynucleic acids of the invention may also include lower eukaryotic cells (like yeasts) or higher eukaryotic cells.

Another embodiment of the invention provides for a recombinant polypeptide encoded by at least part of any of the polynucleic acids of the invention described above, and being expressed in a transformed cellular host as described here above.

Said recombinant polypeptide is also called an "expression product".

The invention further relates to a recombinant polypeptide as described above, with said recombinant polypeptide consisting of a heterologous sequence, provided by the vector, fused in frame to the amino acid sequence of any of the polypeptides of the invention described above or part thereof.

Said recombinant polypeptide fused to a heterologous sequence is also called a "fusion protein". The heterologous sequence may bring about any desired side effect to the resulting fusion protein, e.g. it may optimize the expression, the purification, the immobilization on a surface etc.

The invention also relates to a method for production of a recombinant polypeptide as described above, comprising:
  transformation of an appropiate cellular host with a recombinant expression vector as described above, wherein any of the polynucleic acids of the invention, or part thereof, has been inserted under the control of the appropiate regulatory elements,
  culturing said transformed cellular host under conditions enabling expression of said insert, and
  harvesting and purifying said polypeptide.

In order to carry out the expression of the polypeptides of the invention in bacteria, like E. coli, the above-mentioned steps can be followed according to principles known in the art, as examplified in the Examples section.

The techniques for carrying out the expression of recombinant polypeptides in any of the other hosts as specified above, are also well known in the art of recombinant expression technology.

The invention further relates to an antibody recognizing specifically any of the polypeptides of the invention as described above, with said antibody being possibly a polyclonal antibody, and preferably a monoclonal antibody.

Preferably, said monoclonal antibody of the invention is different from A66/05H01/E09 (Cloeckaert et al., 1991).

A further embodiment of the present invention relates to an antibody, more particularly a monoclonal antibody, characterized in that it is specifically raised against an antigenic determinant of an isolated 17-kDa Brucella polypeptide.

According to an alternative embodiment, the present invention also relates to an antigen-binding fragment of the antibody, said fragment being of the $F(ab')_2$, Fab or single chain Fv type, or any type of recombinant antibody derived from said specific antibodies or monoclonal antibodies.

The terms "antigenic determinant" or "epitope" refer to that portion of a molecule that is specifically bound by an antibody combining site. Antigenic determinants may be determined by any of the techniques known in the art or may be predicted by a variety of computer prediction models known in the art.

The expression "antibody recognizing specifically" means that binding between the antigen as a ligand and a molecule containing an antibody combining site, such as a Fab portion of a whole antibody, is specific, signifying that no cross-reaction occurs.

The expression "antibody specifically raised against a compound" means that the sole immunogen used to produce said antibody was said compound.

Antibodies according to a preferred embodiment of the invention include specific polyclonal antisera raised against the Brucella polypeptides of the invention, and having no cross-reactivity to others proteins, or monoclonal antibodies raised against the Brucella polypeptides of the invention.

The possible crosseactivity of the polyclonal antisera may be eliminated by preabsorption of the polyclonal antiserum against the cross-reacting antigenic determinants.

The monoclonal antibodies of the invention can be produced by any hybridoma liable to be formed according to classical methods from splenic cells of an animal, particularly of a mouse or rat, immunized against the adhesive polypeptides according to the invention, defined above on the one hand, and of cells of a myeloma cell line on the other hand, and to be selected by the ability of the hybridoma to produce the monoclonal antibodies recognizing the polypeptides which have been initially used for the immunization of the animals.

The monoclonal antibodies according to this preferred embodiment of the invention may be humanized versions of the mouse monoclonal antibodies made by means of recombinant DNA technology, departing from the mouse and/or human genomic DNA sequences coding for H and L chains or from cDNA clones coding for H and L chains.

Also fragments derived from these monoclonal antibodies such as Fab, $F(ab)'_2$ and ssFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses.

The antibodies involved in the invention can be labelled by an appropriate label of the enzymatic, fluorescent, or radioactive type.

The invention also relates to the use of the proteins of the invention, muteins thereof, or fragments thereof, for the selection of recombinant antibodies by the process of repertoire cloning (Perrson et al., 1991).

According to a preferred embodiment of the present invention, an antibody, or an antigen-binding fragment $F(ab')_2$, Fab, single chain Fv and all types of recombinant antibodies, as defined above are further characterized in that they can inhibit the infection of Brucella strains to the specific cell type which they infect in vivo.

According to another embodiment, the present invention relates to a monoclonal antibody as defined above, obtainable by a process comprising at least the following steps:

fusing the splenocytes from mice infected with Brucella species together with myeloma cells, and selecting the anti-Brucella hybridomas by means of ELISA and subsequent limiting dilution, selecting the hybridomas producing a monoclonal antibody, specifically directed against any of the 17-kDa Brucella polypeptides by means of ELISA, and, recovering the monoclonal antibodies from ascites fluid or from a culture of the selected hybridomas.

The present invention also relates to a hybridoma producing any of the monoclonal antibodies as defined above.

The present invention further relates to an anti-idiotype antibody raised against any of the antibodies as defined above.

The term "anti-idiotype antibodies" refers to monoclonal antibodies raised against the antigenic determinants of the variable region of monoclonal antibodies themselves raised against the Brucella 17 kDa polypeptides. These antigenic determinants of immunoglobulins are known as idiotypes (sets of idiotopes) and can therefore be considered to be the "fingerprint" of an antibody (for review see de Preval, 1978; Fleishmann and Davie. 1984). The methods for production of monoclonal anti-idiotypic antibodies have been described by Gheuens and McFarlin (1982). Monoclonal anti-idiotypic antibodies have the property of forming an immunological complex with the idiotype of the monoclonal antibody against which they were raised. In this respect the monoclonal antibody is often referred to as Ab1, and the anti-idiotypic antibody is referred to as Ab2. These anti-idiotype Ab2s may be used as substitutes for the polypeptides of the invention or as competitors for binding of the polypeptides of the invention to their target.

The present invention further relates to antisense peptides derived from the Brucella polypeptides as defined above.

More particularly, the term "antisense peptide" is reviewed by Blalock (1990) and by Roubos (1990). In this respect, the molecular recognition theory (Blalock, 1990) states that not only the complementary nucleic acid sequences interact but that, in addition, interacting sites in proteins are composed of complementary amino acid sequences (sense ligand with receptor or sense ligand with antisense peptides). Thus, two peptides derived from complementary nucleic acid sequences in the same reading frame will show a total interchange of their hydrophobic and hydrophilic amino acids when the amino terminus of one is aligned with the carboxy terminus of the other. This inverted hydropathic pattern might allow two such peptides to assume complementary conformations responsible for specific interaction.

The antisense peptides can be prepared as described in Ghiso et al. (1990). By means of this technology it is possible to logically construct a peptide having a physiologically relevant interaction with a known peptide by simple nucleotide sequence analysis for complementarity, and synthesize the peptide complementary to the binding site.

The present invention still further relates to a method for in vitro diagnosis of Brucella (species) infection comprising at least the step of contacting a sample possibly containing anti-Brucella (species) 17-kDa polypeptide antibodies, Brucella (species) 17-kDa antigens and/or Brucella (species) 17 kDa protein encoding nucleic acids, with:

a 17-kDa Brucella polypeptide or peptide as defined above, under conditions allowing the formation of an immunological complex, or, a Brucella 17-kDa polynucleic acid sequence as defined above, under conditions allowing the formation of a hybridization complex, with said nucleic acids of said sample being possibly amplified prior to hybridization, or, an antibody specifically directed against a 17-kDa antigen as defined above, under conditions allowing the formation of an immunological complex, or, an anti-idiotype antibody as defined above, under conditions allowing the formation of an antibody-anti-idiotypic complex, or, an antisense peptide as defined above, under conditions allowing the formation of an antigen-antisense peptide complex, and subsequently detecting the complexes formed.

The Brucella species which may be diagnosed by the above method include *B. abortus, B. melitensis, B. ovis, B. suis.*

The term "sample" may refer to any biological sample (tissue or fluid) containing Brucella nucleic acid sequences, antibodies or polypeptides.

A preferable detection method is the detection of antibodies against Brucella (species), and the preferred sample in that case is serum or plasma.

In a more specific embodiment, the invention relates to a method for detecting antibodies to Brucella (species) present in a biological sample, comprising:

contacting the biological sample to be analysed with any of the polypeptide as described above, under conditions allowing the formation of an immunological complex, and detecting the immunological complex formed between said antibodies and said polypeptide.

Conditions allowing the formation of an immunological complex are known to the person skilled in the art.

In a special embodiment, the polypeptides being used in the above-described method for detection of anti-Brucella species antibodies, can be replaced by anti-idiotype antibodies as described above, acting as their equivalents.

Conditions allowing the formation of an antibody-anti-idiotypic complex are known in the art.

The invention further relates to a method for detecting the presence of Brucella (species) antigens in a biological sample, comprising:

contacting the biological sample to be analysed with an antibody according to the invention, under conditions allowing the formation of an immunological complex, and detecting the immunological complex formed between said antigens and said antibody.

In a special embodiment, the antibodies being used in the above-described method for detection of Brucella antigens, may be replaced by anti-sense peptides as described above, acting as their equivalents.

Conditions allowing the formation of an antigen-antisense peptide complex are known in the art.

Design of immunoassays is subject to a great deal of variation, and many formats are known in the art. Protocols may, for example, use solid supports, or immunoprecipitation. Most assays involve the use of labeled antibody or polypeptide; the labels may be, for example. enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

An advantageous embodiment provides for a method for detection of anti-Brucella (species) antibodies in a sample, whereby the polypeptides of the invention are immobilized on a solid support, eventually on a membrane strip. Different polypeptides of the invention may be immobilized together or next to each other (e.g. in the form of parallel lines). The polypeptides of the invention may also be combined with other antigens from other organisms, belonging to the genus Brucella or to other genera.

The combination of different antigens in one single detection method as described may have certain advantages, such as:

achieving a higher test sensitivity: e.g. by combining several antigenic determinants from Brucella species, the number of positively reacting sera from field infected individuals may be greater, and/or enabling differentiation between individuals infected by different pathogens, belonging to the genus Brucella or to other genera, enabling differentiation between Brucella (species) field-infected and vaccinated individuals.

The invention thus also relates to a solid support onto which the polypeptides of the invention, possibly in combination with other polypeptides, have been immobilized.

Another embodiment of the invention provides for a method for detecting the presence of Brucella (species) polynucleic acids present in a biological sample, comprising:

possibly extracting the polynucleic acids contained in the sample, amplifying the Brucella (species) polynucleic acids with at least one primer as described above, detecting the amplified nucleic acids, possibly after hybridization with a probe as described above.

Conditions allowing hybridization are known in the art and e.g. exemplified in Maniatis et al. (1982). However, according to the hybridization solution (SSC, SSPE, etc.), the probes used should be hybridized at their appropriate temperature in order to attain sufficient specificity (in some cases differences at the level of one nucleotide mutation are to be discriminated).

Amplification of nucleic acids present in a sample prior to detection in vitro may be accomplished by first extracting the nucleic acids present in the sample according to any of the techniques known in the art. In case of extraction of RNA, generation of cDNA is necessary; otherwise cDNA or genomic DNA is extracted.

The amplification methods are detailed above.

Suitable assay methods for purposes of the present invention to detect hybrids formed between oligonucleotide probes according to the invention and the nucleic acid sequences in a sample may comprise any of the assay formats kown in the art. For example, the detection can be accomplished using a dot blot format, the unlabelled amplified sample being bound to a membrane, the membrane being incubated with at least one labelled probe under suitable hybridization and wash conditions, and the presence of bound probe being monitored. Probes can be labelled with radioisotopes or with labels allowing chromogenic or chemiluminescent detection such as horse-radish peroxidase coupled probes.

An alternative is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

According to an advantageous embodiment, the process of detecting Brucella polynucleic acid sequences contained in a biological sample comprises the steps of contacting amplified copies derived from the genetic material, with a solid support on which probes as defined above, have been previously immobilized.

In a very specific embodiment, the probes have been immobilized on a membrane strip in the form of parallel lines. This type of reverse hybridization method is specified further as a Line Probe Assay (LiPA).

The invention thus also relates to a solid support onto which the polynucleotides of the invention have been immobilized.

The invention further relates to a method for detecting individuals having been in contact with Brucella (species), comprising:

contacting a polypeptide according to the invention with the cellular immune system of the individual, either in vitro or in vivo, and detecting and quantifying the cellular immune response raised against said polypeptides.

The above-said cellular immune response can be measured either in vivo, such as a delayed type hypersensitivity reaction upon subcutaneous injection of the polypeptides of the invention, or in vitro, such as stimulation of periferal blood lymphocytes or secretion of interferon-gamma, upon addition of the polypeptides of the invention to a sample of periferal blood lymphocytes under conditions allowing recognition of the polypeptides by the cells responsive for the immune response, conditions which are known to the person skilled in the art.

The invention further relates to a diagnostic kit for the detection of antibodies to Brucella (species) present in a biological sample, said kit comprising any of the polypeptides according to the invention, with said polypeptides being preferably bound to a solid support.

The present invention relates more particularly to a kit for determining the presence of anti-Brucella (species) antibodies as defined above present in a biological sample liable to contain them, comprising:

at least one polypeptide or peptide as defined above, preferentially in combination with other polypeptides or peptides from Brucella, with said polypeptides being preferentially immobilized on a solid substrate, a buffer or components necessary for producing the buffer enabling binding reaction between these polypeptides and the antibodies against the Brucella 17 kDa protein present in the biological sample, means for detecting the immune complexes formed in the preceding binding reaction, possibly also including an automated scanning and interpretation device for inferring the presence of Brucella antibodies in the sample from the observed binding pattern.

The kit according to this aspect of the present invention may comprise in addition to peptide or polypeptide antigens according to the invention, also other Brucella antigenic proteins or peptides known in the art (such as outer membrane protein (OMP) proteins or peptides), or other bacterial antigenic proteins or peptides in general.

In a very specific embodiment the invention relates to a kit for the detection of anti-Brucella species antibodies in a biological sample as described above, whereby the polypeptides of the invention are replaced by the anti-idiotype antibodies as described above.

The invention further relates to a diagnostic kit for the detection of antigens of Brucella (species) present in a biological sample, said kit comprising an antibody as described above, with said antibody being preferably bound to a solid support.

In a very specific embodiment, the invention relates to a diagnostic kit for the detection of antigens of Brucella species present in a biological sample, whereby the antibody as described above is replaced by an antisense peptide.

The invention further also relates to a diagnostic kit for the detection of Brucella (species) polynucleic acids present in a sample, said kit comprising a probe as described above and/or a primer as described above.

According to a preferred embodiment, the present invention relates to a kit for determining the presence of Brucella polynucleic acids as defined above present in a biological sample liable to contain them, comprising:

possibly at least one primer or a set of primers as defined above, at least one oligonucleotide probe as defined above, with said probes being preferentially immobilized on a solid substrate, and more preferentially on one and the same membrane strip, a buffer or components necessary for producing the buffer enabling a hybridization reaction between these probes and the possibly amplified products to be carried out, a solution or components necessary for producing the solution, enabling washing of the hybrids formed under the appropiate wash conditions, means for detecting the hybrids resulting from the preceding hybridization, possibly also including an automated scanning and interpretation device for inferring the Brucella (strain) polynucleic acids present in the sample from the observed hybridization pattern.

According to this advantageous method, the probes are immobilized in a Line Probe Assay (LiPA) format. This is a reverse hybridization format (Saiki et al., 1989) using membrane strips onto which several oligonucleotide probes (including negative or positive control oligonucleotides) can be conveniently applied as parallel lines.

The invention thus also relates to a solid support, preferably a membrane strip, carrying on its surface one or more probes as defined above, coupled to the support in the form of parallel lines.

A LiPA support may contain on its surface different oligonucleotide probes derived from polynucleic acid sequences according to the invention which hybridize specifically with certain strains of Brucella (such as *B. abortus, B. melitensis, B. ovis, B. suis*) or may contain at least one Brucella oligonucleotide probe derived from a polynucleic acid sequence according to the present invention in addition to other Brucella probes or probes derived from other bacterial and/or viral organisms.

The LiPA is a very rapid and user-friendly hybridization test. Results can be read 4 h after the start of the amplification. After amplification during which usually a non-isotopic label is incorporated in the amplified product, and alkaline denaturation, the amplified product is contacted with the probes on the membrane and the hybridization is carried out for about 1 to 1,5 h hybridized polynucleic acid is detected. From the hybridization pattern generated, the Brucella strain can be deduced either visually, but preferably using dedicated software. The LiPA format is completely compatible with commercially available scanning devices, thus rendering automatic interpretation of the results very reliable. All those advantages make the LiPA format liable for the use of Brucella detection in a routine setting. The LiPA format should be particularly advantageous for detecting the presence of different Brucella strains.

The invention further relates to a kit for the detection and quantification of the cellular immune response against Brucella (species) in an individual, said kit comprising any of the polypeptides according to the invention as described above.

A method and kit for diagnosis, based on the quantification of the cellular immune response, as specified above, enables the identification of individuals (humans or ruminants) which have been in contact with the Brucella pathogen. Said contact may subsequently lead to a disease state (=field infected individuals) or to a protected state of the individual (=vaccinated individuals).

According to a preferred embodiment, the present invention relates to a method or a kit for diagnosis of Brucella infection as defined above, further characterized in that said polypeptides, peptides, polynucleic acids, antibodies, anti-idiotypic antibodies or anti-sense peptides are particularly useful for differentiating Brucella (species) field infected individuals from Brucella vaccinated individuals.

The invention further relates to a vaccine composition which provides protective immunity against Brucella (species) infection in a mammal (human, ruminants) comprising as an active principle at least one of the polypeptides according to the invention, or at least one of the polynucleic acid sequences or recombinant vectors according to the invention, said active principle being combined with a pharmaceutically acceptable carrier.

According to a special embodiment, the vaccine composition as described above may comprise as an active principle one of the anti-idiotype antibodies as described above.

Besides the Brucella 17 kDa proteins according to the invention, said vaccine composition may comprise also any other Brucella immunogenic component (such as outer membrane proteins (OMP) Cloeckaert et al. 1991) or any other bacterial or other immunogenic component in general.

In a specific embodiment, polynucleic acid sequences coding for any of the polypeptides as defined above, are used as a vaccine, either as naked DNA or as part of recombinant vectors. In this case, it is the aim that said nucleic acids are expressed into immunogenic protein/peptide and thus confer in vivo protection to the vaccinated host (e.g. Ulmer et al., 1993).

The active ingredients of such a vaccine composition may be administered orally, subcutaneously, conjunctivally, intramuscularly, intranasally, or via any other route known in the art including for instance via the binding to carriers, via incorporation into liposomes, by adding adjuvants known in the art, etc.

According to another embodiment, the current invention also provides for a recombinant Brucella (species) strain in which the gene encoding a Brucella 17-kDa antigen as described above has been deleted or inactivated.

The invention also relates to a vaccine composition which provides protective immunity against Brucella (species) infection in a mammal (human, ruminants) and which enables the differentiation between field infected and vaccinated individuals, said vaccine composition comprising as an active principle a recombinant Brucella (species) strain in which the gene encoding a Brucella 17 kDa antigen has been deleted or inactivated. The present embodiment is illustrated further in Example 7.

The above-described recombinant Brucella strain may be an interesting component of a vaccine composition, providing protective immunity against brucellosis, yet permitting differentiation between Brucella field infected and vaccinated individuals, because of its distinctive immunological signature.

The invention also relates to any of the above-mentioned substances (polypeptides, antibodies, polynucleic acids, anti-idiotype antibodies, antisense peptides) for use as a medicament, more particularly for any of the medical (diagnostic or prophylactic) applications as mentioned above.

Furthermore, the invention relates to the use of any of the above-mentioned substances (polypeptides, antibodies, polynucleic acids, anti-idiotype antibodies, antisense peptides) for the manufacture of a medicament, more particularly for the preparation of a vaccine or for the preparation of a diagnostic composition.

FIGURE AND TABLE LEGENDS

Table 1: Amino acid substitutions which may form the basis of the muteins according to the present invention.

Table 2: Sheep sera and cow sera were tested by Western blot experiments on total *B. melitensis* and *B. abortus* protein extract, respectively. The sheep naturally infected but negative in classical serology were considered positive upon a positive DTH reaction. Ten cows were vaccinated and for 3 of them the vaccination was successful (P), for the other seven animals, protection was not obtained (NP).

Most of these sera were then retested on *B. abortus* total protein extract in competitive ELISA with a monoclonal antibody specific for the 17-kDa antigen. *: number of positive sera (a band at 17 kDa in Western blots or at least 30% inhibition in ELISA).

Table 3: Summary of the seroreactivity of different species (goat, sheep, cattle) with the 17 kDa *Brucella abortus* protein. n=number of animals tested.

FIG. 1 Nucleotide sequence (SEQ ID NO 1) of the 811 bp fragment encoding the 17-kDa *Brucella abortus* protein. The predicted amino acid sequence (SEQ ID NO 2) is shown below the nucleotide sequence. The putative Shine and Delgarno sequence and the stop codon are shown in bold.

FIG. 2 Western blot analysis of *B. melitensis* proteins. Blots were probed with a sheep serum (Lane 1) or with monoclonal antibodies directed against the OMP16.5 as described by Cloeckaert et al. (1991) (A68/04G01/C06, Lane 2) or directed against the 17 kDa protein of this invention (A66/05H01/E09, Lane 3). A: *B. melitensis* total protein extract (rough strain H38, 40 μg/well); B: purified-recombinant OMP16.5 (0.1 μg/well); C: extract from recombinant *E. coli* expressing the 17-kDa antigen (40 μg/well); D: Extract from *E. coli* control strain.

FIG. 3 Protein sequence of the 17-kDa fusion protein as produced in *E. coli* (SEQ ID NO 3). The Brucella sequence is shown in bold.

FIG. 4: Reactivity of a set of individual goat sera on microwells coated with the recombinant 17 kDa *Brucella abortus* antigen. The horizontal line indicates the cutoff value, calculated as the mean of the negative sera plus 3 SD. Negative goat sera were obtained from a region free of brucellosis.

FIG. 5: Reactivity of a set of human sera from Brucella infected patients on microwells coated with the recombinant 17 kDa *Brucella abortus* antigen. The cutoff value was calculated as the mean of the negative sera (blood donors) plus 3 SD.

EXAMPLES

MATERIALS AND METHODS

Reagents. All reagents were of analytical grade and obtained from Merck (Darmstadt, Germany), Sigma (St.

Louis, Mo.), or Bio-Rad Laboratories (Richmond, Calif.). Restriction enzymes and DNA modifying enzymes were purchased from Boehringer Mannheim (Brussels, Belgium) and were used according to the manufacturer's instructions. Protein concentrations were determined by the bicinchoninic acid (Pierce, Rockford, Ill.).

Bacteria and vectors. *E. coli* Y1090, *E. coli* MC1061, *E. coli* DH5 alpha F' competent cells and pBluescript SK+ vector were from Stratagene (La Jolla, Calif.).

Monoclonal antibodies. The monoclonal antibodies (Mabs A66/05H01/E09 and A68/04G01/C06) were prepared as described in Cloeckaert et al., 1990 and Cloeckaert et al., 1991. Ascitic fluids or hybridoma culture supernatants were used.

Sera. Sheep sera were obtained from J. Blasco (Servicio de Investigacion Agraria, Zaragoza, Spain) and cow sera were from the Faculté Universitaire Notre-Dame de la Paix (FUNDP). One hundred sera from naturally *B. melitensis*-infected sheep and 36 cow sera from naturally *B. abortus*-infected animals with a positive classical serology for Brucella infection (Alton et al., 1988) were used. Twenty sheep sera from infected animals which had a negative serology but a positive DTH reaction were also included. Sera from experimentally vaccinated and infected cows were obtained as follows. Pregnant heifers (10 animals) were vaccinated subcutaneously with *B. abortus* strain B19 ($150 \times 10^6$ CFU). At 88 days post-vaccination, the heifers were conjunctively infected with $16.6 \times 10^6$ *B. abortus* strain 544. Animals were bled 135 days post-infection. Fifteen sheep sera and 14 cow sera from healthy animals were used as controls. Successful vaccination was proven by the absence of infection of the heifers and of the new born calves.

Preparation of bacterial protein extracts. Total protein extract from *B. melitensis* strain H38R (depleted in high molecular weight lipopolysaccharide) was kindly provided by G. Dubray (INRA, Nouzilly, France). Briefly, the bacteria were grown on solid agar, collected by washing and heated at 95° C. for 1 h in Laemmli buffer (Laemmli, 1970) containing 2% SDS. Total protein extract from *B. abortus* 45/20 rough strain were grown in liquid medium, centrifuged and treated as above. Total protein extract from recombinant *E. coli* was obtained from 5 ml overnight culture (O.D. at 600 nm=1) in Luria broth medium (L. B., Maniatis et al., 1982) supplemented with 0.1 g/l ampicillin and 1% glucose. Bacteria were centrifuged for 10 min at 5,000×g. The pellet was resuspended in 1 ml of electrophoresis sample buffer (Laemmli, 1970), heated at 100° C. for 5 min. and centrifuged.

Recombinant *B. abortus* minor outer membrane protein (OMP). The OMP16.5 gene (Tibor et al., 1994) was expressed in *E. coli* as a fusion protein with a mTNF leader peptide (25 amino acids, Van Gelder et al., 1993) and between the mTNF and the OMP, a cluster of 6 histidine residues was inserted to allow purification of the fusion protein by immobilized metal-ion affinity chromatography (IMAC, Hochuli et al., 1988). The fusion protein was purified to at least 99% homogeneity, as determined by gel electrophoresis followed by silver staining (unpublished results). Due to this fusion, this recombinant protein migrated at an apparent molecular weight of 20 kDa in SDS-PAGE.

Construction of a *B. abortus* genomic library. The lambda gtl 1 *B. abortus* genomic library was generously provided by Dr. P. de Wergifosse (Université catholique de Louvain, Belgium, de Wergifosse, 1992). It was prepared by Sau3A digestion of *B. abortus* chromosomal DNA. The sticky ends were filled-in, and EcoR1 linkers were added to insert the DNA fragments into the lambda gt11 EcoR1 cloning site. General molecular biological techniques were performed as described by Maniatis et al. (1982).

Library plating and immunoscreening. A bacteriophage suspension (10 µl) in phage dilution buffer (20 mM Tris, 100 mM NaCl, 10 mM magnesium sulfate, pH 7.4) was incubated (20 min at 37° C.) with an overnight culture (0.6 ml) of *E. coli* Y1090, grown at 37° C. in LB and supplemented with 0.1 g/l ampicillin, 10 mM magnesium sulfate and 2% maltose. Thirty ml of top agar (LB+0.7% agar+0.1 g/l ampicillin+10 mM magnesium sulfate) prewarmed at 48° C., was then added to the mixture and immediately plated onto a 220×220 mm Petri dish containing 150 ml of solid medium (LB containing 1.2% agar). After plating, the dishes were left for 5 h at 37° C. and subsequently covered with a nitrocellulose membrane (Hybond-C; Amersham, Brussels, Belgium), wetted in a 10 mM isopropyl β-D-thiogalactopyranoside (IPTG) solution, and blotted dry between two sheets of 3 MM Whatman paper. After overnight incubation (37° C.), the membrane was peeled off and saturated for 1 h at room temperature with 5% fat-free milk in a Tris salt buffer (TBS) pH 7.4 containing 0.05% NP40 (TBS is 10 mM Tris and 150 mM NaCl). All subsequent incubations were also performed at room temperature. Sera from *B. melitensis*-infected sheep were diluted 1/40 in TBS-NP40 buffer, containing 5% fat-free milk and *E. coli* MC1061 lysate (diluted to 1 mg/ml of protein content) and the mixture was incubated with the membrane for 90 min. After 3 washes in TBS-NP40, a rabbit anti-sheep alkaline phosphatase conjugate (Jackson, West Grove, Pa.) diluted 1/5000 in TBS-NP40 was added to the membrane for a 1 h incubation. After 3 more washes, bound antibody was revealed with NBT/BCIP (0.37 mM each) in a Tris buffer pH 9.5 (0.1 M Tris, 0.1 M NaCl, 5 mM magnesium sulfate) for 10 min. A positive plaque was removed from the top agar with a sterile tip and suspended in 100 µl phage dilution buffer. The positive bacteriophage was replated several times until plaque lifts showed more than 99% immunoreactive plaques.

Gel electrophoresis and Western blotting. The total bacterial protein extracts (40 µg/well) were analyzed by SDS-PAGE (12.5%) in the presence of β-mercapto ethanol as described by Laemmli (Laemmli, 1970). Proteins were transferred by semi-dry Western blotting (Tsang et al., 1983) (transfer buffer: 25 mM Tris, 192 mM glycine, 20% methanol) to nitrocellulose for 40 min at 0.8 mA per $cm^2$. The membrane was saturated with 5% fat-free milk as describe above and incubated overnight with monoclonals or sera. Ascites were diluted 1/1,000 in TBS-NP40 containing 5% fat-free milk and sera were diluted 1/40 in TBS-NP40 containing 5% fat-free milk and *E. coli* lysate (final *E. coli* protein concentration: 1 mg/ml). After 3 washes, bands were revealed with rabbit anti-mouse IgG conjugate (Prosan, Denmark), rabbit anti-sheep conjugate (as described above) or rabbit anti-cow conjugate (1/5000, Sigma, St Louis, Mo.).

Competitive ELISA. Sonicated cell extract of *B. abortus* (strain 45/20) was coated on microplates (69620, Nunc) at 20 µg/ml in 5 fold diluted buffer (GBS: 0.17 M NaCl, 0.1 M glycine and 6 mM $NaN_3$, pH 9.2). After saturation with casein hydrolysate, twofold diluted sera and Mab ascite (1/10,000), in a GBS buffer supplemented with 50 mM EDTA and 0.1% Tween-20 (GBS-EDTA-Tw), were incubated for 1 h at room temperature in the microwells. The binding of the Mab was revealed by 1 h incubation at room temperature with a sheep anti-mouse peroxidase-conjugate (Amersham, Brussels, Belgium) diluted 1/1000 in GBS-EDTA-Tw containing 4% casein hydrolysate. Reagents in excess were removed between each step by 6 washings with a 0.15 M NaCl solution containing 0.01% Tween-20. O-Phenylenediamine (0.4% wt/vol) with 2 mM $H_2O_2$ in a citrate-phosphate buffer (0.05 M $Na_2HPO_4$, 0.025 M citric acid, pH 5) was used to develop the assay. The signal was read at 490 nm and 630 nm and the difference was recorded using a BIO kinetics Reader EL-340 (Bio-tek instruments, inc., Vermont, USA). A reduction in signal of more than 30% relative to the serum free control, was considered as a positive competition reaction.

Colony blotting. Recombinant *E. coli* colonies grown on solid medium were transferred by colony blotting to a nitrocellulose disc prewetted in PBS (135 mM NaCl, 10 mM $Na_2HPO_4$, 1 mM $KH_2PO_4$, 5 mM KCl, pH 7.4). The filter was gently shaken in a solution containing PBS with 0.5% Tween-20 for 30 min at room temperature to lyse the bacteria. The membrane was subsequently rinsed twice with TBS-NP40 and the immunoscreening was performed as described above.

Polymerase Chain Reaction (PCR; Mullis & Falnoona, 1987). The *B. abortus* DNA insert was recovered from the purified bacteriophage by PCR directly on the isolated bacteriophage. With lambda gt11 primers (Stratagene, La Jolla, Calif.) the following conditions were used: The reaction mixture (50 $\mu$tl) contained 0.1 M PFU of recombinant phage, 100 pmol of each primer, 200 mM of each dNTP (Pharmacia, Uppsala Sweden), 1 unit of Taq polymerase (Cetus, Emeryville, Calif.) with the appropriate buffer. The reaction mixture was heated for 5 min at 95° C. and then 40 cycles (95° C., 55° C. and 72° C., 1 min each) were performed in a thermocycler (Perkin Elmer Cetus, Emeryville, Calif.). To terminate, a 10 min elongation step at 72° C. was added.

Cloning. DNA fragments, obtained by EcoR1 or HindIII digestion, were cloned in a pBluescript SK+ vector (SK+, Stratagene, La Jolla, Calif.) and plasmids were transformed and propagated in *E. coli* DH5 alpha F'. Plasmid purification was performed on a QIAGEN matrix (Diagen, Germany) as described by the manufacturer.

Nucleic acid sequencing. Sequence analysis of the DNA fragments cloned in SK+ plasmids was performed using the chain termination procedure (Sanger et al., 1977), adapted to allow analysis on an automated DNA sequencer (Applied Biosystems, Foster city, Calif.). Sequencing reactions were carried out using the dye-terminator technology, as described by the manufacturer, using the universal or reverse M13 primers. In order to obtain the complete sequence of the fragment, 2 internal oligonucleotides were custom synthesized (Phamacia, Uppsala, Sweden) to enable internal priming. Sequence manipulations were performed using the Intelligenetics software package (California, USA).

Example 1

Cloning and Sequencing of the *B. abortus* Gene Encoding a 17-kDa Antigen Identification of a New Gene In a first screening, about 35,000 gt11 plaques of the lambda gt11 *B. abortus* genomic library (prepared as described in the Materials and Methods section) were probed with a pool of field sera from *B. melitensis*-infected sheep. One positive plaque was identified and purified by repeated plating. The purified bacteriophage was again plated and the plaques were probed with different Mabs directed to *B. abortus* proteins by means of an immunoscreening as described in the Materials and Methods section (Cloeckaert et al., 1990, 1991). One Mab (A66/05H01/E09) clearly yielded a strong signal with the selected phage. To recover the DNA fragment, the purified bacteriophage was used as template in a PCR reaction with primers flanking the cloning site. A 1500-bp DNA fragment was obtained and purified via agarose gel electrophoresis (10). After EcoR1 digestion, 2 bands of about 800 and 700 bp, respectively, appeared on agarose gel (data not shown). Both fragments were cloned and expressed separately in the SK+ vector. The recombinant bacteria were then analyzed for the presence of an antigen reactive with the Mab cited above. Only the 800-bp insert produced a protein which was immunologically reactive with the Mab A66/05H01/E09 as shown by colony blotting. The protein was produced irrespective of IPTG induction of the culture.

Sequence analysis. By treatment of the 800-bp insert fragment with HindIll, two fragments of 425 bp and 375 bp, respectively, were obtained. The fragments were cloned in a SK+ vector as EcoR1-HindIII fragments and sequenced on both strands. The sequence crossing the HindIII site was obtained using internal primers on the parental 800 bp fragment. On one strand, an 463-bp open reading frame (ORF) was identified (FIG. 1). The calculated molecular weight of the encoded protein (17.3 kDa) matched very well with the size observed on Western blot (FIG. 2). A Shine and Delgarno consensus sequence (GAGGA) was found upstream from the putative initiation codon (position −8). A consensus promoter sequence, as described for Brucella genes (12), was not found in the 290-bp upstream from the ORF which are present in the cloned fragment.

Data bank analysis. A homology search was completed for the 158 amino acid sequence as shown in FIG. 1 using the Swiss-Prot 27 (all entries) and the PIR 38 (all entries) Data Banks. This homology search on the protein level confirmed that the 17 kDa Brucella abortus protein as depicted in SEQ ID NO 2 was new. The closest related proteins found in this search had a homology of only 36% over the 158 amino acid sequence. Data Bank homology analysis of the nucleotide sequence (SEQ ID NO 1) revealed a homology of only 35% with the closest known sequence (EMBL36; EMBL-nl1011,

Example 2

Production of Recombinant 17-kDa Antigen in *E. Coli*

2.1. Construction of recombinant vector producing the 17-kDa antigen.

The 800 bp fragment (example 1) was recovered from the SK+ vector by PCR using two primers designed to allow the directional cloning in the expression vector pIGFH10. This vector enables expression of heterologous proteins in *E. coli* as fusion proteins with a short mouse tumor necrosis factor (mTNF) peptide. Moreover, the vector also confers a polyhistidine sequence of six consecutive histidine residues to the fusion protein, allowing fast and efficient purification using immobilized metal ion affinity chromatography (IMAC).

The primer used at the 5'-end was 5'CGTGAGGATCCTATGAACCAAAGC3' (SEQ ID NO 4), whereas the 3'-end primer was 5'GAGTTCTAGACAAGCGCGGCGATGC3' (SEQ ID NO 5). The first contains a BamH1 site and the latter an Xba1 site (both in bold) for cloning in the same sites of the expression vector pIGFH10. In this way a reading frame fusion between the ORF of the 17 kDa protein and the mTNF-His6 leader peptide is obtained.

The expected fusion protein will contain 37 amino acids provided by the vector and 158 amino acids from the Brucella gene. The sequence of the expected protein is given in FIG. 3.

2.2. *E. Coli* Expression of the 17-kDa Protein.

The transcription of the heterologous gene cloned in the expression vector pIGFH10 is controlled by the early rightward lamba promoter (Pr) and is controlled by the C1 repressor. When an *E. coli* strain containing a compatible plasmid with the C1-857 mutant gene encoding a temperature sensitive variant of the C1 repressor is used, the expression of the heterologous gene can be initiated by shifting the culture from 28° C. to 42° C. For these experiments, the strain MC1061 [pAC1] was used.

This strain was transformed with the expression plasmid and grown at 28° C. For induction experiments, an overnight culture was diluted 1/100 in fresh medium containing tetracyclin (10 μg/ml) and grown to a density of 0.200 measured at 600 nm.

The temperature was then shifted to 42° C. and incubation was continued for several hours. At 1 hour intervals, a sample was taken from the culture for analysis of the expression level. The samples were analysed on PAGE and western blot using Mab A66/05H01/E09.

From these experiments, the conditions for large scale fermentation of the culture were determined. A 15L fermentation was then performed using an induction time of 2 hours. The cells were collected by low speed centrifugation and the pellet was stored at −70° C. until further use.

2.3. Purification of the 17-kDa Fusion Protein.

The cell pellet was thawed and resuspended in 125 ml of lysis buffer (10 mM TrisHCl, 100 mM KCl, 5 mM EDTA, 25 mM aminocaproic acid, 2 mM PMSF, 1 mM DTT at pH 6.8) and passed twice through a French press. After centrifugation (27,000 g for 20 min at 4° C.) the pellet was washed with 125 ml Triton X-100 buffer (25 mM TrisHCl, 0.05% Triton X-100, pH 6.8) and again centrifuged in the same conditions as above. The pellet obtained was then solubilised in 6M guanidinium chloride buffer (75 ml) (0.1 M Phosphate, 0.05% Triton X-100 at pH 6.5). After clearing at 30.000 g for 30 min at 4° C., the solution was loaded on an IMAC column activated with $NiCl_2$ as described by the manufacturer (Pharmacia) and equilibrated with the same 6M guanidinium chloride buffer. The extract was loaded on the column at room temperature at a flow of 4 ml/min. A 30 ml gelbed was used for 37 ml of the extract, containing 18 mg protein per ml. The column was washed with the 6M guanidinium chloride buffer until the absorption measured at 280 nm decreased. Bound proteins were then eluted with a pH gradient starting at pH 6.5 down to 3.7 (450 ml) and 7 ml fractions were collected.

The eluted proteins were analysed by SDS PAGE and coomassie staining. The 17-kDa protein obtained was estimated to be more than 95% pure and from 2 column runs about 350 mg protein was obtained, as estimated by the BCA method (Pierce) using bovine serum albumine as standard. The protein thus obtained was used in competition ELISA assays to study the reaction with Brucella positive sera. Alternatively, this protein was also used in indirect ELISA to determine the anti-Brucella antibodies present in the sample (see Example 6).

Example 3

Western Blotting of the Recombinant 17-kDa Protein

Figure 2:
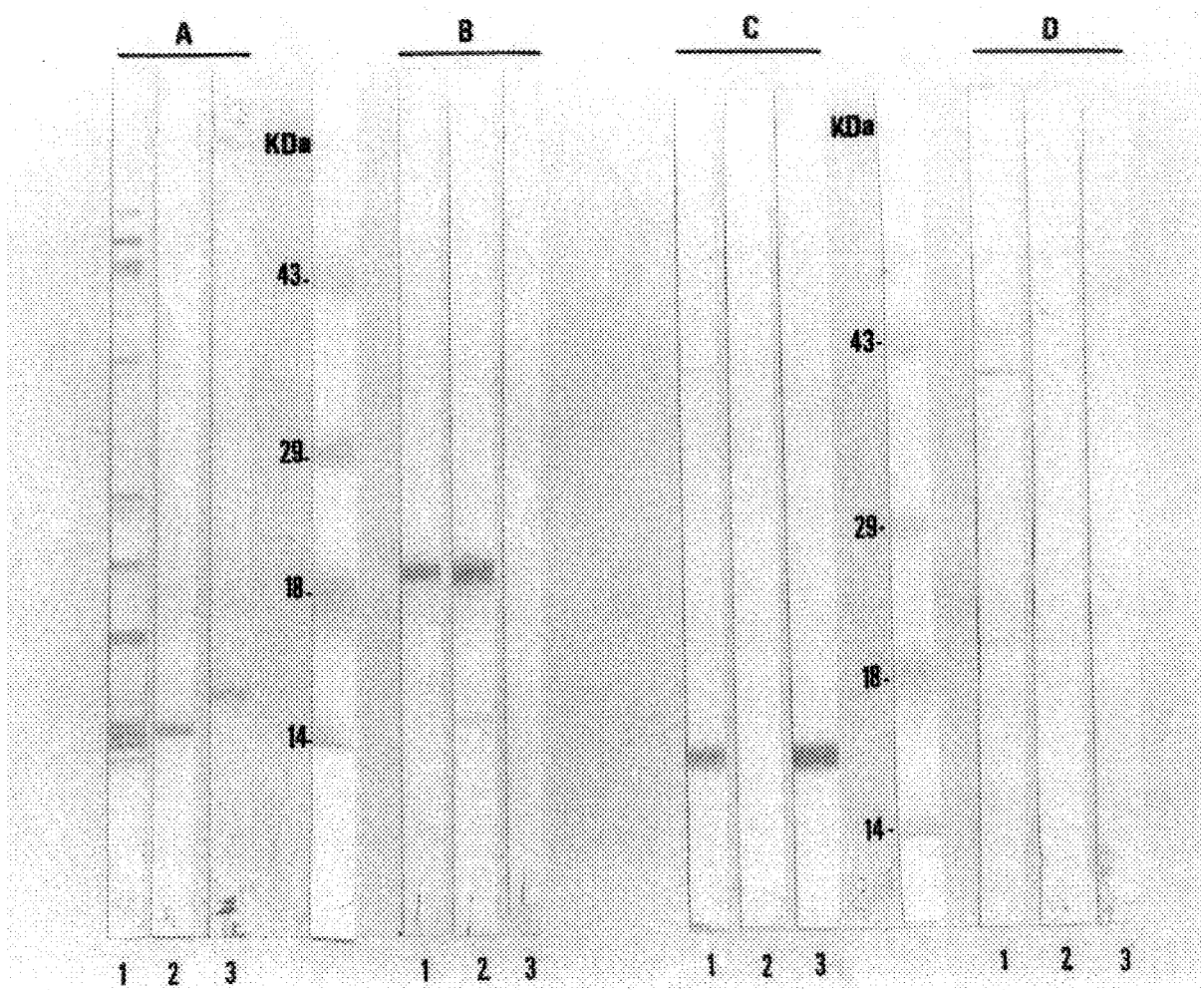

Western blotting analysis of the protein expressed by the recombinant bacteriophage, containing the above-sequenced region, with Mab A66/05H01/E09 showed that the immunoreactive protein migrated as a 17-kDa molecule (FIG. 2/A3C3). When Mab A66/05H01/E09 was used to develop Western blots prepared with lysate from *B. melitensis* the same protein of 17 kDa was revealed (FIG. 2/A3,C3). Another Mab (A68/04G01/C06) known to reveal a 16.5 kDa outer membrane protein (OMP16.5) from *B. abortus* was also used to probe Western blot strips containing the new recombinant 17-kDa antigen as well as another recombinantly produced fusion protein OMP16.5 (Tibor et al., 1994) and *B. melitensis* extract. This experiment clearly indicates that the latter monoclonal did not recognize the new 17-kDa antigen, whereas good reactivity with the recombinant OMP 16.5 was observed as well as with the Brucella extract (FIG. 2/A2,B2,C2). The D series contains extract from *E. coli* cells, not expressing Brucella proteins and probed with the same antibodies.

Example 4

Western Blot Analysis of *B. melitensis*-infected Sheep Sera and *B. abortus* Infected Cattle Sera To evaluate the significance of the 17-kDa antigen of the present invention for diagnostic purposes, Western blot experiments were performed with sera from field-infected animals. These sheep and cattle sera, positive in classical serology, were tested on *B. melitensis* or *B. abortus* total protein extract respectively, using Western blot analysis.

From *B. melitensis*-infected sheep, 100 sera which are positive in classic standard serology and 20 sera from animals with a negative serology but a positive DTH reaction, were analyzed by Western blotting on *B. melitensis* (H38, R strain) total protein extract. Each serum identified up to 14 bands in the range 10 kDa to 97 kDa (data not shown). In general, more bands with a higher intensity were revealed in the case of the serologically positive sera than in the case of the serologically negative samples. Out of the 100 and 20 sera mentioned above, 51% and 20% respectively of these sera showed a band at 17 kDa (Table 2). On the other hand, 36 *B. abortus* field-infected cow sera were analyzed by Western blotting on *B. abortus* (45/20 R strain) total protein extract. Each serum was reactive with up to 12 bands in the range 9 kDa to 97 kDa (data not shown). Thirty-nine percent of these 36 sera showed a band at 17 kDa (Table 2). None of the 15 sheep sera nor the 14 cow sera from healthy animals gave a signal in the 17 kDa region upon Western blot analysis.

At the 17-kDa position, a serologically reactive minor outer membrane protein (OMP16.5) is also present. This protein is distinct from the 17-kDa antigen described in the present invention by its reactivity towards Mabs as well as by its primary sequence (Tibor et al., 1994).

To assess the reaction of the sera with the 17 kDa protein (to ensure that the reactivity was not due to the OMP16.5), 20 sheep sera and 4 cow sera, randomly chosen from those with a positive serology, and which react at 17 kDa in Western blots of Brucella extracts, were retested by Western blotting on a total protein extract from a recombinant *E. coli* expressing the 17-kDa antigen. Seventy percent (14 sera) of the sheep sera and 75% (3 sera) of the cow sera were positive on the recombinant *E. coli* produced protein (data not shown), indicating that most of the reactivity seen at the 17 kDa position can be attributed to reaction with the newly identified protein of the invention. In addition, out of 10 control sheep sera and 6 control cow sera, none were reactive with the *E. coli* produced protein.

From experiments with vaccinated animals, preliminary results indicate that serological response towards this new 17-kDa antigen may be absent in B19-vaccinated and protected animals whereas it is present in animals infected upon challenge. This is an important property which enables the use of the antigen in differential serology.

Examnple 5

Competition ELISA of Field-infected Sheep and Cow Sera with Mab A66/05H01/E09

Fifty sera from field-infected sheep showing reactivity with Brucella antigens on Western blots, including 23 of which did not react with the 17-kDa protein on Western blots, were tested in a competition ELISA with the Mab A66/05H01/E09. Seventy percent (35 sera) were positive in this test, including 12 samples which showed no reactivity at the 17 kDa position on Western blots. Out of the 20 sera from infected sheep with a negative serology but with a positive DTH reaction, 20% could still be detected by this test. In the same conditions, the 36 sera from field-infected cows were tested: sixty-one percent were positive in competitive ELISA even if only 39% had shown a band at 17 kDa (Table 2). Prom the 10 vaccinated animals, 6 were protected from subsequent infection, only 3 of which gave healthy calves. The sera from the three latter heifers did not react in competition ELISA, whereas sera from the other heifers (7 animals) were positive in competition ELISA after the experimental infection (Table 2). All sera were negative between vaccination and infection. The specificity of the reaction was assessed with 10 sheep sera and 6 cow sera from healthy animals, all of which were negative. Furthermore, 2 sera from *Yersinia enterocolitica* O:9-infected cows and 2 sera from Salmonella urbana-infected cows were also negative in the competition ELISA test (data not shown).

Example 6

Indirect ELISA with Recombinantly Produced Brucella 17 kDa Fusion Protein.

The purified recombinant fusion protein (Example 2) was used to coat microwells (NUNC maxisorp) by diluting the protein to a final concentration of 3 µg/ml in phosphate buffered saline pH 6.0. From this solution, 100 µl was added to each well and incubated for 1 h at 37° C. The wells were then blocked with 0.1% casein solution (blocking buffer) for 1 h at 37° C. and further incubated with 100 µl of the sera to be tested, diluted 1/100 in blocking buffer. Bound antibodies were revealed with a species specific peroxidase conjugated rabbit antibody directed to the Fc part of the IgG. The latter was obtained from DAKO (Denmark) and diluted 1/5000 before use. Substrate and TMB chromophore were then added (200 µl) and after 30 min at room temperature the reaction was stopped with 50 µl 2N sulfuric acid. The absorption was measured at 600 nm in an automated ELISA reader.

Figure 4:
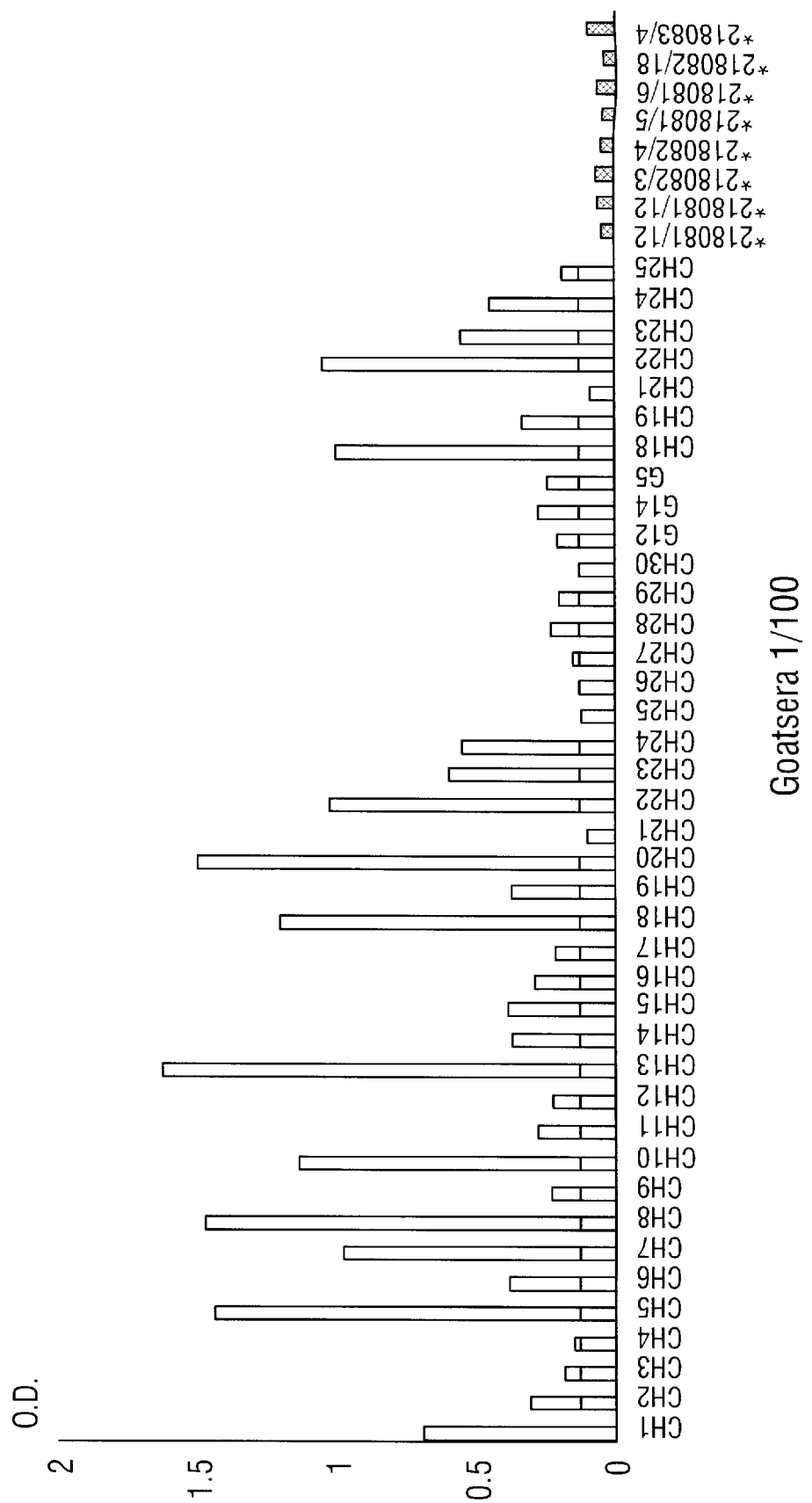
Figure 5:
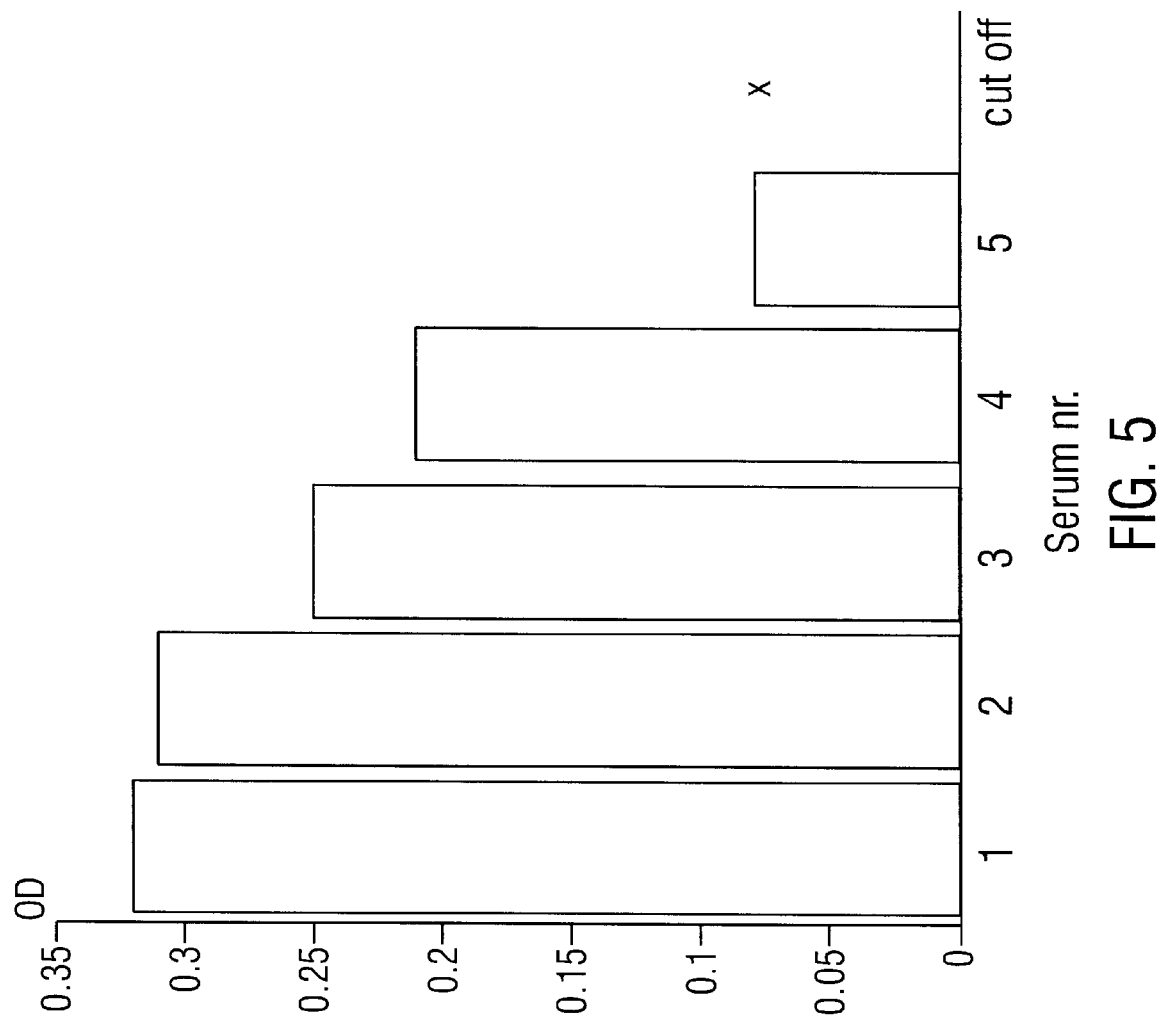

The results shown in FIG. 4 show that for goat sera of animals infected with Brucella, 88% of the animals are reactive with the 17 kDa fusion protein. For a limited number of human sera tested, a significant fraction also reacted with the 17 kDa protein (FIG. 5). For sheep sera, the fraction reactive with the 17 kDa protein is variable, depending on the origin of the sera and for cattle, about 45% of infected animals are reactive with the protein. The latter is the highest score ever found with a Brucella protein antigen in Brucella field infected cattle.

Table 3 below summarizes the results for the different species tested.

| Species | Fraction reactive (%) |
| --- | --- |
| Goats | 88 (n = 48) |
| Sheep | 37–80 (n > 200) |
| Cattle | 45 (n = 35) |

Example 6

Construction of Brucella 17-kDa Gene Deletion Mutants for Vaccine Purposes

Identification of proteins of interest for diagnosis could be followed by the construction of Brucella vaccinal strains deleted for at least one of these antigens, assuming that they are essential neither for bacterial survival nor for protection. Diagnosis based on these proteins would enable the discrimination between vaccinated and infected animals.

6.1. Deletion Strategy

The deletion implies a double homologous recombination event leading to the replacement of the resident wild type gene ORF (open reading frame) by a genetic marker. Disruption of the gene of interest by insertion of a genetic marker does not prevent expression of a truncated protein from the disrupted gene. This expression may lead to misinterpretation of the mutant phenotype. It is therefore preferred to construct mutants with a completely deleted gene, which can be achieved by an ORF replacement protocol. The choice of the genetic marker, bioluminescence luxAB gene, will be discussed also.

6.1.1. Choice of a Genetic Marker for Vaccine Strain

The construction of a vaccine strain implies not only a controlled attenuation of the virulence but also the introduction of an appropriate genetic label. Since an antibiotic-resistance marker is an undesirable feature in a vaccinal strain, the use of a genetic marker like the luxAB gene encoding the luciferase from *Vibrio harveyi* can be envisaged. The luciferase system is a potentially powerful tool for use in studying the survival of genetically engineered bacterial strains in animals and in the environment. This marker, integrated into the chromosome, has been used to monitor the survival of engineered *Y. enterocolitica* in murine and bovine feces (Kaniga et al, 1991).

6.1.2. Principles of the Deletion Strategy.

Reverse genetics, based on homologous recombination, has been greatly facilitated by the use of vectors unable to replicate in the host where mutations are to be introduced. A ColE1-derived plasmid is not maintained in Brucella species (Halling et al, 1991) and is therefore useful as suicide vector.

A ColE1 based suicide vector containing the Brucellia DNA insert where the ORF of interest has been replaced by a genetic marker will be introduced in a recipient Brucelta bacteria by conjugation with an *E. coli* donor. A mobilizable suicide vector as well as a mobilizing *E. coli* donor strain are necessary for conjugation to take place. These mobilizing *E. coli* have integrated in their chromosome the transfer genes of the broad host range plasmid RP4 (Simon et al, 1983) and the vector will contain the RK2 origin of transfer (Selvaraj et al, 1984).

By a single homologous recombination between chromosomal and incoming ORF flanking regions, plasmid insertion into the chromosomal DNA occurs. This results in an integrant diploid for the flanking regions of the gene of interest. Integrants are obtained by selecting for the vector-borne antibiotic-resistance marker, for example the neomycin-kanamycin phosphotransferase gene encoding kanamycin resistance.

A second homologous recombination event is necessary for plasmid excision but can result in a wild type genotype, i. e. it leaves a wild type gene copy in the Brucella chromosome or, on the other hand, can lead to a mutant chromosome. Since the genetic marker used to replace the ORF (luxAB) is not a selectable marker, this second event can only be detected by screening for the loss of Kan selection marker. This procedure is limiting when the frequency of the second crossing-over is low. To avoid such an efficiency decrease, one can take advantage of positive selection of double recombinants using the sacB gene of *Bacillus subtilis* as described by Kaniga and coll. in 1992 (gene sacB, regulated in cis by the sequence sacR, encodes levan sucrase that catalyses hydrolysis of sucrose as well as synthesis of levans).These authors have designed a mobilizable suicide vector containing the sacB selectable marker that allows easy construction of unmarked mutations in Gram bacteria species where the expression of sacB gene in presence of sucrose is lethal. sacB turned out to be an efficient counter-selection marker of the double recombination.

Before functional studies are conducted, the deletion mutant has to be further characterized by southern- and immuno-blotting to ensure that the deletion event has taken place as expected.

TABLE 1

| Amino acids | Synonymous groups |
|---|---|
| Ser (S) | Ser, Thr, Gly, Asn |
| Arg (R) | Arg, His, Lys, Glu, Gln |
| Leu (L) | Leu, Ile, Met, Phe, Val, Tyr |
| Pro (P) | Pro, Ala, Thr, Gly |
| Thr (T) | Thr, Pro, Ser, Ala, Gly, His, Gln |
| Ala (A) | Ala, Pro, Gly, Thr |
| Val (V) | Val, Met, Ile, Tyr, Phe, Leu, Val |
| Gly (G) | Gly, Ala, Thr, Pro, Ser |
| Ile (I) | Ile, Met, Leu, Phe, Val, Tyr |
| Phe (F) | Phe, Met, Tyr, Ile, Leu, Trp, Val |
| Tyr (Y) | Tyr, Phe, Trp, Met, Ile, Val, Leu |
| Cys (C) | Cys, Ser, Thr, Met |
| His (H) | His, Gln, Arg, Lys, Glu, Thr |
| Gln (Q) | Gln, Glu, His, Lys, Asn, Thr, Arg |
| Asn (N) | Asn, Asp, Ser, Gln |
| Lys (K) | Lys, Arg, Glu, Gln, His |
| Asp (D) | Asp, Asn, Glu, Gln |
| Glu (E) | Glu, Gln, Asp, Lys, Asn, His, Arg |
| Met (M) | Met, Ile, Leu, Phe, Val |

TABLE 2

| | Sheep sera | | | Cattle sera | | | |
|---|---|---|---|---|---|---|---|
| | Field infection | | | | | | |
| | Posit. serol. | DTH posit. | Healthy | Field inf. posit. serol. | Experim. Infect. | | Healthy |
| | | | | | P | NP | |
| Western blot | | | | | | | |
| # sera tested | 100 | 20 | 15 | 36 | 3 | 7 | 6 |
| # posit (%)* | 51 (51) | 4 (20) | 0 (0) | 14 (39) | 0 (0) | 5 (71) | 0 |
| Competit. ELISA | | | | | | | |
| # sera tested | 50 | 20 | 10 | 36 | 3 | 7 | 6 |
| # positive (%)* | 35 (70) | 4 (20) | 0 (0) | 22 (61) | 0 (0) | 7 (100) | 0 |

REFERENCES

Alton, G. G., L. M. Jones, R. D. Angus, and J. M. Verger. 1988. Techniques for brucellosis laboratory. Institut National de la Recherche agronomique, (Ed.) Paris.

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad. Sci. USA 81(11):3297–301.

Blalock J (1990) Complementarity of peptides specified by 'sense' and 'antisense' strands of DNA. Trends Biotechnol. 8: 140–144.

Cloeckaert, A., P. de Wergifosse, G. Dubray, and J. N. Limet. 1990. Identification of seven surface-exposed Brucella outer membrane proteins by use of monoclonal antibody immunogold labelling for electron microscopy and enzyme linked immunosorbent assay. Infect. Immun. 58:3980–3987.

Cloeckaert, A., Jacques, I., Bosseray, N., Limet, J. N., Bowden, R., Dubray, G. and Plommet, M. 1991. Protection conferred on mice by monoclonal antibodies directed against outer membrane protein antigens of Brucella. J. Med. Microbiol. 34, 175–180.

Corbel, M. F., F. A. Stuart, and R. A. Brewer. 1983. Observations of serological cross-reaction between smooth Brucella species and organisms of other genera. Dev. Biol. Stand. 56:341–363.

de Préval (1978) Immunoglobulins, In: Bach J Immunology, New York, Wiley and Sons: 144–219.

de Wergifosse, P. 1992. Analyse génétique et immunologique de deux proteines de la membrane externe de *B. abortus*: l'OMP25 et l'OMP36. These de Doctorat soutenue à l'Université Catholique de Louvain (Belgique), Faculté des Sciences.

Fekete, A., J. A. Bantle, S. M. Hailing, and R. W. Stich. 1992. Amplification fragment length polymorphism in Brucella strains by use of polymerase chain reaction with arbitrary primers. J. Bacteriol. 174:7778–7783.

Fensterbank, R. 1984. Le diagnostic allergique des brucelloses animales. Dev. Biol. Stand. 56:401405.

Ficht, T. A., S. W. Bearden, B. A. Sowa, and L. G. Adams. 1989. A 36 kDa *B. abortus* cell envelope protein is encoded by repeated sequences closely linked in the genomic DNA. Infect. Immun. 56:2036–2046.

Ficht, T. A., S. W. Bearden, B. A. Sowa, and L. G. Adams. 1989. DNA sequence and expression of the 36 kDa outer membrane protein gene of *B. abortus*. Infect. Immun. 57:3281–3291.

Fleishmann J, Davie J (1984) Immunoglobulins: allotypes and idiotypes. In: Paul W (Ed) Fundamental Immunology. New York, Raven Press: 205–220.

Goldbaum, F. A., J. Leoni, J. C. Wallach, and C. A. Fossali. 1993. Characterization of an 18 kDa Brucella cytoplasmic protein which appears to be a serological marker of active infection of both human and bovine brucellosis. J. Clin. Microbiol. 31:2141–2145.

Gheuens J, Mc Farlin D (1982) Use of monoclonal anti-idiotypic antibody to P3-X6Ag8 myeloma protein for analysis and purification of B lymphocyte hybridoma products. Eur J Immunol 12: 701–703.

Ghiso J, Saball E, Leoni J, Rostagno A, Frangion (1990) Binding of cystatin C to C4: the importance of antisense peptides and their interaction. Proc Natl Acad Sci (USA) 87: 1288–1291.

Halling S M, Detilleux P G, Tatum F M, Judge B A and Mayfield J E. 1991. Deletion of the BCSP31 gene of *Brucella abortus* by replacement. Infect. Immun. 59, 3863–3868.

Hochuli E., W. Bannwarth, H. Döbeli, R. Gentz, and D. St über. 1988. Genetic approach to facilitate purification of recombinant proteins with a novel metal chelate adsorbent. Biotechnology, 6:1321–1325.

Kaniga K, Sory M P, Delor I, Saegerman C, Limet J N, Cornelis G R. 1992. Monitoring of *Yersinia enterocolitica* in murine and bovine faeces on the basis of the chromosomally integrated luxAB marker gene. Appl. Env. Microbiol. 58, 1024–1026.

Kaniga K, Delor I and Cornelis G R. 1991. A wide host range suicide vector for improving reverse genetics in gram negative bacteria: inactivation of the blaa gene of *Yersinia enterocolitica*. Gene, 109, 137–141.

Laemmli, U. K. 1970. Cleavage of structural proteins during the assembly of the head of bacteriophage T4. Nature (London) 227:680–685.

Maniatis, T., E. F. Fritsch, and J. Sambrook. 1982. Molecular cloning. A laboratory manuel. Cold Spring Harbor Laboratory, Cold Spring Harbor, N.Y.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human imniunodeficiency virus. Proc. Nati. Acad. Sci. USA 84(21):7706–10.

Mayfield, J. E., B. J. Bricker, H. Godfrey, R. M. Crosby, D. J. Knignht, S. M. Halling, D. Balinsky, and L. B. Tabatabai. 1988. The cloning, expression, and nucleotide sequence of a gene coding for an immunogenic *Brucella abortus* protein. Gene, 63:1–9.

Miller P, Yano J, Yano E, Carroll C, Jayaram K, Ts'o P (1979) Nonionic nucleic acid analogues. Synthesis and characterization of dideoxyribonucleoside methylphosphonates. Biochemistry 18(23):5134–43.

Mullis, K. B., and F. A. Falnoona. 1987. Specific synthesis of DNA in vitro via a polymerase-catalyzed reaction. Methods Enzymol. 155:335–350.

Nielsen P, Egholm M, Berg R, Buchardt O (1991) Sequence-selective recognition of DNA by strand displacement with a thymine-substituted polyamide. Science 254(5037): 1497–500.

Nielsen P, Egholm M, Berg R, Buchardt O (1993) Sequence specific inhibition of DNA restriction enzyme cleavage by PNA. Nucleic-Acids-Res. 21(2): 197–200.

Perry, M. B., and D. R. Bundle. 1990. Antigenic relationships of the lipopolysaccharides of *E. hermannii* strains with those of *E. coli* 0157: H7, *B. melitensis* and *B. abortus*. Infect.Immun. 58:1391–1395.

Roubos E (1990) Sense-antisense complementarity of hormone receptor interaction sites. Trends Biotechnol 8: 279–281.

Sanger, F., S. Nicklen, and A. S. Coulson. 1977. DNA sequencing with chain-terminating inhibitors. Proc. Natl. Acad. Sci. USA 74:5463–5467.

Schoerner, C., K. Wartenberg, and M. Röllinghoff. 1990. Differentiation of serological responses to *Y. enterocolitica* O9 and Brucelia species by immunoblot or ELISA using whole bacteria and Yersinia outer membrane proteins. J. Clin. Microbiol. 28:1570–1574.

Selvaraj G, Fong Y C, Iyer V N. 1984. A portable DNA sequence carrying the cohesive site (cos) of bacteriophage lambda and the mob (mobilization) region of the broad-host-range plasmid RK2: a module for the construction of new cosmids. Gene 32, 235–241.

Simon R, Priefer U and Pühler H (1983) Biotechnology, 784–791.

Tibor et al. (1994) Molecular cloning, nucleotide sequence and occurrence of a 16.5 kDa outer membrane protein of *Brucella abortus* with similarity to PAL lipoprotein. Infect. Immun., 62, 3633–3639.

Tsang, V. C. W., J. N. Peralta, and A. R. Simons. 1983. Enzyme linked immunoelectrotransfer blot techniques (EITB) for studying by gel electrophoresis. Methods Enzymol. 92:377–391.

Ulmer J, Donnelly J, Parker S, et al. 1993. Heterologous protection against influenza by injection of DNA encoding a viral protein. Science, 259: 1745–1749.

Van Gelder, P., F. Bosman, F. de Meuter, H. van Heuverswyn, and P. Herion. 1993. Serodiagnostic of toxoplasmosis by using a recombinant form of the 54 kDa rhoptry antigen expressed in *E. coli*. J. Clin. Microbiol. 31:9–15.

Verger, J. M., F. Grimont, P. A. D. Grimont, and M. Grayon. 1985. Brucella, a monospecific genus as shown by deoxyribonucleic acid hybridization. Int. J. Syst. Bacteriol. 35:979–989.

Verstraete, D. R., and A. J. Winter. 1984. Comparison of SDS- PAGE profiles and antigenic relatedness among outer membrane proteins of 49 *B. abortus* strains. Infect. Immun. 46:182–187.

Zygmunt, M. S., F. B. Gilbert, and G. Dubray. 1992. Purification, characterization, and seroactivity of a 20 kDa Brucella protein antigen. J. Clin. Microbiol. 30:2662–2667.

What is claimed is:

1. An isolated polypeptide wherein the amino acid sequence of the isolated polypeptide has at least 70% identity to the 158 residue amino acid sequence as shown in SEQ ID NO 2.

2. The isolated polypeptide of claim 1, wherein the amino acid sequence of the isolated polypeptide has at least 80% identity to the 158 residue amino acid sequence as shown in SEQ ID NO 2.

3. The isolated polypeptide of claim 1, wherein the amino acid sequence of the isolated polypeptide has at least 90% identity to the 158 residue amino acid sequence as shown in SEQ ID NO 2.

4. An isolated *Brucella abortus* polypeptide which corresponds to an amino acid sequence as shown in SEQ ID NO 2 or SEQ ID NO 3.

* * * * *

SEQUENCE LISTING

```
<160> NUMBER OF SEQ ID NOS:  8

<210> SEQ ID NO 1
<211> LENGTH: 811
<212> TYPE: DNA
<213> ORGANISM: Brucella abortus
<220> FEATURE:
<221> NAME/KEY: CDS
<222> LOCATION: (290)..(763)

<400> SEQUENCE: 1
gaattccgat cagtgcatag tttccgcgtg ctcgcgcaat ggtgcgcggg cttgttctcg       60
gggcggggtg aaactcccca ccggcggtat gaaaagcaat tttcaagccc gcgagcgcct      120
gaaatggaag ccgattcgca tgccatttca gggtcagcag atccggtgag atgccggagc      180
cgacggttaa agtccggatg gaagagagcg aatgagcgtc acgattgcgc cttccggcgt      240
cgttcttgcg ttcttttgtg cgccctgatt ctagtttcgt gaggaacct atg aac caa      298
                                                       Met Asn Gln
                                                         1
```

-continued

```
agc tgt ccg aac aag aca tcc ttt aaa atc gca ttc att cag gcc cgc      346
Ser Cys Pro Asn Lys Thr Ser Phe Lys Ile Ala Phe Ile Gln Ala Arg
      5                  10                  15 tgg cac gcc gac atc gtt gac gaa gcg cgc aaa agc ttt gtc gcc gaa      394
Trp His Ala Asp Ile Val Asp Glu Ala Arg Lys Ser Phe Val Ala Glu
 20                  25                  30                  35 ctg gcc gca aag acg ggt ggc agc gtc gag gta gag ata ttc gac gtg      442
Leu Ala Ala Lys Thr Gly Gly Ser Val Glu Val Glu Ile Phe Asp Val
                 40                  45                  50 ccg ggt gca tat gaa att ccc ctt cac gcc aag aca ttg gcc aga acc      490
Pro Gly Ala Tyr Glu Ile Pro Leu His Ala Lys Thr Leu Ala Arg Thr
             55                  60                  65 ggg cgc tat gca gcc atc gtc ggt gcg gcc ttc gtg atc gac ggc ggc      538
Gly Arg Tyr Ala Ala Ile Val Gly Ala Ala Phe Val Ile Asp Gly Gly
         70                  75                  80 atc tat cgt cat gat ttc gtg gcg acg gcc gtt atc aac ggc atg atg      586
Ile Tyr Arg His Asp Phe Val Ala Thr Ala Val Ile Asn Gly Met Met
     85                  90                  95 cag gtg cag ctt gaa acg gaa gtg ccg gtg ctg agc gtc gtg ctg acg      634
Gln Val Gln Leu Glu Thr Glu Val Pro Val Leu Ser Val Val Leu Thr
100                 105                 110                 115 ccg cac cat ttc cat gaa agc aag gag cat cac gac ttc ttc cat gct      682
Pro His His Phe His Glu Ser Lys Glu His His Asp Phe Phe His Ala
                120                 125                 130 cat ttc aag gtg aag ggc gtg gaa gcg gcc cat gcc gcc ttg cag atc      730
His Phe Lys Val Lys Gly Val Glu Ala Ala His Ala Ala Leu Gln Ile
            135                 140                 145 gtg agc gag cgc agc cgc atc gcc gcg ctt gtc tgactaaccc tctataatac    783
Val Ser Glu Arg Ser Arg Ile Ala Ala Leu Val
        150                 155 gcccgcaatg ggtataaatg tcgaattc                                        811

<210> SEQ ID NO 2
<211> LENGTH: 158
<212> TYPE: PRT
<213> ORGANISM: Brucella abortus

<400> SEQUENCE: 2

Met Asn Gln Ser Cys Pro Asn Lys Thr Ser Phe Lys Ile Ala Phe Ile
  1               5                  10                  15

Gln Ala Arg Trp His Ala Asp Ile Val Asp Glu Ala Arg Lys Ser Phe
             20                  25                  30

Val Ala Glu Leu Ala Ala Lys Thr Gly Gly Ser Val Glu Val Glu Ile
        35                  40                  45

Phe Asp Val Pro Gly Ala Tyr Glu Ile Pro Leu His Ala Lys Thr Leu
     50                  55                  60

Ala Arg Thr Gly Arg Tyr Ala Ala Ile Val Gly Ala Ala Phe Val Ile
 65                  70                  75                  80

Asp Gly Gly Ile Tyr Arg His Asp Phe Val Ala Thr Ala Val Ile Asn
                 85                  90                  95

Gly Met Met Gln Val Gln Leu Glu Thr Glu Val Pro Val Leu Ser Val
            100                 105                 110

Val Leu Thr Pro His His Phe His Glu Ser Lys Glu His His Asp Phe
        115                 120                 125

Phe His Ala His Phe Lys Val Lys Gly Val Glu Ala Ala His Ala Ala
    130                 135                 140

Leu Gln Ile Val Ser Glu Arg Ser Arg Ile Ala Ala Leu Val
145                 150                 155
```

```
<210> SEQ ID NO 3
<211> LENGTH: 195
<212> TYPE: PRT
<213> ORGANISM: Artificial Sequence
<220> FEATURE:
<223> OTHER INFORMATION: Description of Artificial Sequence:SYNTHETIC
      CONSTRUCT

<400> SEQUENCE: 3

Met Val Arg Ser Ser Gln Asn Ser Ser Asp Lys Pro Val Ala His
 1               5                  10                  15

Val Val Ala Asn His Gln Val Glu Glu Gln Gly Ile His His His
            20                  25                  30

His His Val Asp Pro Met Asn Gln Ser Cys Pro Asn Lys Thr Ser Phe
        35                  40                  45

Lys Ile Ala Phe Ile Gln Ala Arg Trp His Ala Asp Ile Val Asp Glu
 50                  55                  60

Ala Arg Lys Ser Phe Val Ala Glu Leu Ala Ala Lys Thr Gly Gly Ser
 65                  70                  75                  80

Val Glu Val Glu Ile Phe Asp Val Pro Gly Ala Tyr Glu Ile Pro Leu
                 85                  90                  95

His Ala Lys Thr Leu Ala Arg Thr Gly Arg Tyr Ala Ala Ile Val Gly
            100                 105                 110

Ala Ala Phe Val Ile Asp Gly Gly Ile Tyr Arg His Asp Phe Val Ala
        115                 120                 125

Thr Ala Val Ile Asn Gly Met Met Gln Val Gln Leu Glu Thr Glu Val
130                 135                 140

Pro Val Leu Ser Val Val Leu Thr Pro His His Phe His Glu Ser Lys
145                 150                 155                 160

Glu His His Asp Phe Phe His Ala His Phe Lys Val Lys Gly Val Glu
                165                 170                 175

Ala Ala His Ala Ala Leu Gln Ile Val Ser Glu Arg Ser Arg Ile Ala
            180                 185                 190

Ala Leu Val
        195

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:SYNTHETIC
      PRIMER

<400> SEQUENCE: 4
cgtgaggatc ctatgaacca aagc                                          24

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:SYNTHETIC
      PRIMER

<400> SEQUENCE: 5
gagttctaga caagcgcggc gatgc                                         25

<210> SEQ ID NO 6
```

```
-continued

<211> LENGTH: 11
<212> TYPE: PRT
<213> ORGANISM: Brucella abortus

<400> SEQUENCE: 6

Ile Ala Phe Ile Gln Ala Asp Asp Val Leu Lys
 1               5                  10

<210> SEQ ID NO 7
<211> LENGTH: 9
<212> TYPE: PRT
<213> ORGANISM: Brucella abortus
<220> FEATURE:
<221> NAME/KEY: VARIANT
<222> LOCATION: (7)..(9)
<223> OTHER INFORMATION: Xaa = Any Amino Acid

<400> SEQUENCE: 7

Ser Gly Tyr Ile Phe Asp Xaa Pro Gly
 1               5

<210> SEQ ID NO 8
<211> LENGTH: 14
<212> TYPE: PRT
<213> ORGANISM: Brucella abortus
<220> FEATURE:
<221> NAME/KEY: VARIANT
<222> LOCATION: (6)..(14)
<223> OTHER INFORMATION: Xaa = Any Amino Acid

<400> SEQUENCE: 8

Gly Val Glu Ala Ala Xaa Ala Ala Leu Gln Ile Val Ser Glu
 1               5                  10
```